US007790689B2

(12) United States Patent
Verma et al.

(10) Patent No.: US 7,790,689 B2
(45) Date of Patent: Sep. 7, 2010

(54) MONOSACCHARIDE DERIVATIVES

(75) Inventors: Ashwani Kumar Verma, Delhi (IN); Sanjay Malhotra, New Delhi (IN); Sankaranarayanan Dharmarajan, Gurgaon (IN); Abhijit Ray, New Delhi (IN); Rajkumar Shirumalla, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 11/755,164

(22) Filed: May 30, 2007

(65) Prior Publication Data
US 2007/0287673 A1 Dec. 13, 2007

(30) Foreign Application Priority Data
May 30, 2006 (IN) .................... 1310/DEL/2006

(51) Int. Cl.
A61K 31/7008 (2006.01)
A61K 31/7012 (2006.01)
A61K 31/34 (2006.01)
C07H 5/04 (2006.01)
C07H 5/06 (2006.01)
C07D 323/02 (2006.01)
C07D 317/00 (2006.01)

(52) U.S. Cl. .................... 514/25; 514/462; 536/4.1; 536/17.5; 549/435; 549/439

(58) Field of Classification Search ........................ None
See application file for complete search history.

(56) References Cited

U.S. PATENT DOCUMENTS

| | | | | |
|---|---|---|---|---|
| 4,017,608 | A | 4/1977 | Gordon | |
| 4,251,520 | A | 2/1981 | Bruzzese et al. | 424/180 |
| 4,849,512 | A | 7/1989 | Tokizawa et al. | 536/4.1 |
| 4,996,195 | A | 2/1991 | Ronsen et al. | 514/23 |
| 5,010,058 | A | 4/1991 | Ronsen et al. | 514/23 |
| 5,298,494 | A | 3/1994 | Arora et al. | 514/23 |
| 5,360,792 | A | 11/1994 | Arora et al. | 514/23 |
| 5,360,794 | A | 11/1994 | Arora | 514/25 |
| 5,367,062 | A | 11/1994 | Arora et al. | 514/25 |
| 6,329,344 | B1 | 12/2001 | Arora et al. | 514/25 |
| 6,590,085 | B1 | 7/2003 | Arora et al. | 536/17.2 |
| 2002/0173632 | A1 | 11/2002 | Boldi et al. | 536/18.7 |
| 2003/0114362 | A1 * | 6/2003 | Gruner et al. | 514/8 |

FOREIGN PATENT DOCUMENTS

| | | |
|---|---|---|
| EP | 0 404 136 | 12/1990 |
| EP | 1 842 855 | 10/2007 |
| FR | 2323392 | 4/1977 |
| FR | 2735130 | 12/1996 |
| JP | 62-051618 | 3/1987 |
| WO | WO 92/04359 | 3/1992 |
| WO | WO 93/13117 | 7/1993 |
| WO | WO 94/03185 | 2/1994 |
| WO | WO 94/11381 | 5/1994 |
| WO | WO 94/28910 | 12/1994 |
| WO | WO 00/42053 | 7/2000 |
| WO | WO 03/029263 | 4/2003 |
| WO | WO2006/111783 | * 10/2006 |
| WO | WO 2006/111783 | 10/2006 |

OTHER PUBLICATIONS

Majumdar et al., "Thiourea: A Novel Cleaving Agent for 1,3-Dioxolanes" Journal of Organic Chemistry (1999) vol. 64 pp. 5682-5685.*
The Merck Manual of Diagnosis and Therapy, Seventeenth Edition, published 1999 by Merck Research Laboratories, pp. 397-398, 948-949, 1916, 1979-1981.*
Merriam-Webster's Collegiate Dictionary, Tenth Edition, published 1998 by Merriam-Webster, Incorporated, p. 924.*
Marone et al., "Pharmacological modulation of human mast cells and basophils", *Clinical & Experimental Allergy*, 32(12):1682-1689 (2002).
Rossi and Olivieri, "Does the Mast Cell Still Have a Key Role in Asthma?", *Chest*, 112(2):523-529 (1997).
Solomon, "Hong Kong, 1894: the role of James A Lowson in the controversial discovery of the plague bacillus", *The Lancet*, 350:59-62 (1997).
Iuvone et al., "Evidence that mast cell degranulation, histamine and tumour necrosis factor α release occur in LPS-induced plasma leakage in rat skin", *British Journal of Pharmacology*, 128:700-704 (1999).
Tigani et al., "Airway hyperresponsiveness to adenosine induced by lipopolysaccharide in Brown Norway rats", *British Journal of Pharmacology*, 136(1):111-119 (2002).
Brown et al., "Role of mast cells, neutrophils and nitric oxide in endotoxin-induced damage to the neonatal rat colon", *British Journal of Pharmacology*, 123:31-38 (1998).
Tunon-de-Lara et al., "Mast Cells in Airway Smooth Muscle", *The New England Journal of Medicine*, 347(13):1040 (2002).

(Continued)

Primary Examiner—Eric S Olson
Assistant Examiner—Geeta Kadambi

(57) ABSTRACT

The present invention relates to monosaccharide derivatives as anti-inflammatory agents. The compounds disclosed herein can be useful for inhibition and prevention of inflammation and associated pathologies including inflammatory and autoimmune diseases such as bronchial asthma, rheumatoid arthritis, type I diabetes, multiple sclerosis, allograft rejection, psoriasis, inflammatory bowel disease, ulcerative colitis, acne, atherosclerosis, cancer, pruritis and allergic rhinitis. Pharmacological compositions containing compounds disclosed herein and the methods of treating bronchial asthma, chronic obstructive pulmonary disease, rheumatoid arthritis, multiple sclerosis, type I diabetes, psoriasis, allograft rejection, inflammatory bowel disease, ulcerative colitis, acne, atherosclerosis, cancer, pruritis, allergic rhinitis and other inflammatory and/or autoimmune disorders, using the compounds are also provided.

2 Claims, No Drawings

OTHER PUBLICATIONS

Polosa et al., "Evolving concepts on the value of adenosine hyper-responsiveness in asthma and chronic obstructive pulmonary disease", *Thorax*, 57:649-654 (2002).

Wood et al., "Fundamentals of neurogastroenterology", *Gut*, 45(Suppl. II):II6-II16 (2002).

Beckman, "How Immune System Gangs Up on Joints", *Science*, 297(5587):1626-1627 (2002).

Supajatura et al., "Differential responses of mast cell Toll-like receptors 2 and 4 in allergy and innate immunity", *The Journal of Clinical Investigation*, 109(10):1351-1359 (2002).

Greene, T.Q. and Wuts, P.G.M., 1991. *Protective Groups in Organic Synthesis*. 2nd Edition. New York: Wiley Interscience Publications.

Hatzelmann and Ullrich, "Regulation of 5-lipoxygenase activity by the glutathione status in human polymorphonuclear leukocytes", *European Journal of Biochemistry*, 169:175-184 (1987).

Hatzelmann and Schudt, "Anti-Inflammatory and Immunomodulatory Potential of the Novel PDE4 Inhibitor Roflumilast in Vitro", *The Journal of Pharmacology and Experimental Therapeutics*, 297(1):267-279 (2001).

Aharony and Stein, "Kinetic Mechanism of Guinea Pig Neutrophil 5-Lipoxygenase", *The Journal of Biological Chemistry*, 261(25):11512-11519 (1986).

Tatsuta et al., "Total synthesis of tylonolide, an aglycone of tylosin", *Tetrahedron Letters*, 22(40):3997-4000 (1981).

Kinoshita et al., "Synthetic studies of amphotericin B. III. An enantiospecific synthesis of the C(1)-C(19) segment of the amphotericin B aglycon", *Bulletin of the Chemical Society of Japan*, 61(6):2147-2156 (1988), Abstract.

Huang et al., "Building Blocks for Oligonucleotide Analogues with Dimethylene Sulfide, Sulfoxide, and Sulfone Groups Replacing Phosphodiester Linkages", *Journal of Organic Chemistry*, 56(12):3869-3882 (1991).

Svoboda et al., "Potential anti-inflammatory agents based on indomethacin esters", *Cesko-Slovenska Farmacie*, 40(2):71-74 (1991), Abstract.

Garcia Fernández et al., "Influence of intramolecular hydrogen-bonding on the conformation of 3-deoxy-3-thioureido sugars", *Carbohydrate Research*, 286:55-65 (1996).

Turks, "Synthesis of protected 3-C-aminomethyl-allose from a methylenenitro derivative", *Rigas Tehniskas Universitates Zinatniskie Raksti, Serija 1: Materialzinatne un Lietiska Kimija*, 1:136-141(2000), Abstract.

Rosenthal and Baker, "Branched-Chain N-Sugar Nucleosides. I. Nucleosides of Branched-Chain Cyanomethyl, Aminoethyl, and N,N-Dimethylcarbamoylmethyl Allo Sugars. 6-N,N-Dimethylamino-9-[3'-C-(N,N-dimethylcarbamoylmethyl)-3'-deoxy-β-D-Allofuranosyl] purine", *Journal of Organic Chemistry*, 38(2):193-197 (1973), Abstract.

Yoshimura et al., "Aminosugars. XXII. Syntheses and Properties of 6-Deoxy-6- and 3-Deoxy-3-guanidino-D-hexoses", *Bulletin of the Chemical Society of Japan*, 47(5):1219-1223 (1974).

Tsang and Wong, "Inhibitors of Tyrosine Kinase Signaling Cascade Attenuated Antigen Challenge of Guinea-Pig Airways in Vitro", *American Journal of Respiratory and Critical Care Medicine*, 162(1):126-133 (2000).

Rosenthal and Shudo, "New Route to Branched-Chain Sugars. Photoamidation and Photohydroxyaklylation of 3-Deoxy-1,2:5,6-di-0-isopropylidene-α-D-*erythro*-hex-3-enofuranose", *Journal of Organic Chemistry*, 37(10):1608-1612 (1972), Abstract.

Fernandez, et al., "Influence of Intramolecular Hydrogen-Bonding on the Conformation of 3-deoxy-3-thioureido Sugars" *Carbohydrate Research*, 286, 55-65 (1996).

* cited by examiner

MONOSACCHARIDE DERIVATIVES

CROSS-REFERENCE TO RELATED APPLICATIONS

This application claims priority to foreign patent application 1310/DEL/2006, filed May 30, 2006 in India.

FIELD OF THE INVENTION

The present invention relates to monosaccharide derivatives as anti-inflammatory agents. The compounds disclosed herein can be useful for inhibition and prevention of inflammation and associated pathologies including inflammatory, cancer, cardiovascular and autoimmune diseases such as bronchial asthma, rheumatoid arthritis, type-I diabetes, multiple sclerosis, allograft rejection, psoriasis, inflammatory bowel disease, ulcerative colitis, acne, atherosclerosis, pruritis or allergic rhinitis. Pharmacological compositions containing compounds disclosed herein and the methods of treating diseases such as bronchial asthma, rheumatoid arthritis, type-I diabetes, multiple sclerosis, cancer, cardiovascular diseases, allograft rejection, psoriasis, inflammatory bowel disease, ulcerative colitis, acne, atherosclerosis, pruritis or allergic rhinitis and other inflammatory and/or autoimmune disorders, using the compounds are also provided.

BACKGROUND OF THE INVENTION

Inflammation is a key defense mechanism of the body that is activated as a result of tissue injury. The inflammatory process is self-containing, however, under certain pathophysiological conditions the inflammatory process tends to perpetuate itself, giving rise to chronic inflammatory diseases like bronchial asthma, rheumatoid arthritis, etc.

Although the exact cellular and molecular bases of most chronic inflammatory disease remain unclear, it has become apparent that several inflammatory cells act in concert towards initiation and perpetuation of an inflammatory response by releasing a wide range of chemokine, cytokine, proteolytic enzymes and other bioactive molecules. Mast cells primed by lymphocytes interact with environmental allergens and release mediators like histamine, prostaglandin, leukotrienes etc. (*Clin. Exp. Allergy* 32:1682, 2002) to initiate an early inflammatory response. This is followed by a delayed inflammatory response due to release of cytokines (IL-4, IL-5, IL-6, IL-8, IL-13, GM-CSF and TNF-alpha), chemokines and proteolytic enzymes (chymase, tryptase) (*Chest* 112: 523, 1997; *Lancet* 350:59, 1997) that not only bring about tissue damage, but attract other inflammatory cells and initiate tissue fibrosis, and the cycle continues. Eosinophils infiltrate inflamed tissue following allergen-mast cell interaction in bronchial asthma and allergic rhinitis. Evidence is emerging that mast cells also interact with bacterial endotoxins leading to generation of cytokines like TNF-alpha, that encourage neutrophil influx into the site of inflammation (*Br. J. Pharmacol.*, 123:31, (1998); *Br. J. Pharmacol.*, 128:700, (1999); *Br. J. Pharmacol.*, 136:111,(2002); *J. Clin. Invest.*, 109:1351,(2002)). Involvement of mast cells in the inflammatory response of chronic obstructive pulmonary disease (*New Eng. J. Med.*, 347:1040,(2002); *Thorax*, 57:649,(2002)), inflammatory bowel disease (*Gut.*, 45,Suppl. II6,(1999)) as well as in rheumatoid arthritis (*Science*, 297: 1626,(2002)), pathologies with prominent neutrophilic inflammation, has been proposed.

U.S. Pat. No. 6,329,344 B1 discloses several monosaccharide derivatives said to be useful as cell adhesion inhibitors. It generally relates to substituted pentose and hexose monosaccharide derivatives, which are said to exhibit cell adhesion inhibitory and anti-inflammatory activities. U.S. Pat. No. 6,590,085 B1 discloses several monosaccharide derivatives described as inhibitors of cell adhesion and cell adhesion mediated pathologies, including inflammatory and autoimmune diseases. U.S. Patent Application 2002/0173632 A1 discloses furanose and amino furanose compounds reportedly useful for rheumatoid arthritis, immunomodulatory diseases inflammatory and proliferative diseases. U.S. Pat. No. 5,298,494 discloses derivatives of monosaccharides, which are said to exhibit anti-proliferative and/or anti-inflammatory activity and are useful for treating mammals having inflammatory disorders and/or autoimmune disorders. U.S. Pat. No. 4,996,195 discloses derivatives of α-D-glucofuranose and α-D-allofuranose described as useful for treating animals and mammals with inflammatory and/or autoimmune disorders.

WO 93/13117 and U.S. Pat. No. 5,360,792 discloses 5- or 6-deoxy hexose monosaccharides having a saturated nitrogen containing heterocycle described as useful as anti-proliferative and anti-inflammatory compounds. WO 94/28910 discloses 5,6-dideoxy-5-amino derivatives of idose and 6-deoxy-6-amino derivatives of glucose, which reportedly exhibit immunomodulatory, anti-inflammatory and anti-proliferative activity. WO 94/11381 discloses derivatives of pentose monosaccharides described as useful as anti-proliferative and anti-inflammatory compounds. U.S. Pat. No. 5,010,058 discloses 3,5,6-disubstituted derivatives of 1,2-O-isopropylidene-α-O-glucofuranoside described as useful for treating inflammatory and autoimmune disorders. U.S. Pat. No. 4,849,512 discloses 3-acylamino-3-deoxyallose derivatives. U.S. Pat. No. 5,367,062 discloses disubstituted and deoxy disubstituted derivatives of α-D-lyxofuranosides reportedly having anti-inflammatory and anti-proliferative activity. U.S. Pat. No. 5,360,794 discloses disubstituted derivatives of α-D-mannofuranoside reportedly having anti-inflammatory and anti proliferative activity. WO 03/029263 discloses 3-deoxy-3-amide derivatives of carbohydrates described as useful as inducers of erythroid cell differentiation. French Patent 2735130 discloses regiospecific synthesis of carbamic polyesters.

SUMMARY OF THE INVENTION

Monosaccharide derivatives which can be used for the inhibition and prevention of inflammation and associated pathologies, including inflammatory, cancer, cardiovascular and autoimmune diseases such as bronchial asthma, rheumatoid arthritis, type-I diabetes, multiple sclerosis, allograft rejection, psoriasis, inflammatory bowel disease, ulcerative colitis, acne, atherosclerosis, pruritis or allergic rhinitis are described herein. Pharmaceutically acceptable salts, pharmaceutically acceptable solvates, enantiomers, diastereomers or N-oxides of these compounds having the same type of activity are also provided. Pharmaceutical compositions containing the compounds, and which may also contain pharmaceutically acceptable carriers or diluents, which may be used for the treatment of inflammatory, cancer, cardiovascular and autoimmune diseases such as bronchial asthma, rheumatoid arthritis, type-I diabetes, multiple sclerosis, allograft rejection, psoriasis, inflammatory bowel disease, ulcerative colitis, acne, atherosclerosis, pruritis or allergic rhinitis are provided herein.

Other aspects will be set forth in accompanying description which follows and in part will be apparent from the description or may be learnt by the practice of the invention.

In accordance with one aspect, there are provided compounds having the structure of Formula I

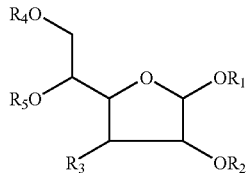

Formula I and their pharmaceutically acceptable salts, pharmaceutically acceptable solvates, esters, enantiomers, diastereomers, N-oxides, polymorphs, metabolites.

$R_1$ and $R_2$ can together form a five-membered acetal, wherein the carbon atom joining the oxygens can be substituted with $R_L$ and $R_m$ [wherein $R_L$ and $R_m$ are independently selected from hydrogen, alkyl, alkenyl, alkynyl, cycloalkyl, aryl, or aralkyl; or $R_L$ and $R_m$ can together join to form a 3-8 membered ring, wherein the ring may optionally contain one or more heteroatoms selected from O, N or S, and the ring may be optionally substituted with one or more of alkyl, alkenyl, alkynyl, amino, substituted amino, cycloalkyl, oxo, hydroxy, carboxy, —$COQR_6$ (wherein Q is O or NH and $R_6$ is selected from alkyl, alkenyl, alkynyl, aryl, aralkyl, and cycloalkyl), alkoxy, aryloxy, halogen (F, Cl, Br, I), aryl, aralkyl, heteroaryl, heterocyclyl, heteroarylalkyl, or heterocyclylalkyl; or $R_L$ and $R_m$ can together join to form an oxo group].

$R_3$ can be

A) —$(CH_2)_nG$ wherein n is an integer from 0-5 and G is selected from
  1) $OR_e$ {wherein $R_e$ is selected from
    a) acyl (with the proviso that n cannot be 0), and
    b) —$C(=O)NR_fR_q$ [wherein $R_f$ and $R_q$ can be independently selected from hydrogen, hydroxy (with the restriction that both $R_f$ and $R_q$ cannot both be hydroxy), alkyl, alkenyl, alkynyl, cycloalkyl, aryl, aralkyl, heteroaryl, heterocyclyl, and $S(O)_2R_7$ (wherein $R_7$ is selected from alkyl, alkenyl, alkynyl, cycloalkyl, aryl, aralkyl, heteroaryl, heterocyclyl, heterocyclylalkyl, heteroarylalkyl, and optionally substituted amino)]; and $R_f$ and $R_q$ may also together join to form a heterocyclyl ring; also, when n is zero, then $R_f$ and $R_q$ cannot be hydrogen, alkyl, alkenyl, alkynyl, cycloalkyl and $R_f$ and $R_q$ together cannot join to form a heterocyclyl ring};
  2) —$NR_jC(=O)OR_s$ (wherein $R_j$ is selected from hydrogen, lower ($C_1$-$C_6$) alkyl, lower ($C_2$-$C_6$) alkenyl, lower ($C_2$-$C_6$) alkynyl, lower ($C_3$-$C_6$) cycloalkyl, aryl, heteroaryl (with the proviso that the heteroaryl ring is not linked through a heteroatom), aralkyl ($C_1$-$C_4$), heteroarylalkyl ($C_1$-$C_4$), and heterocyclylalkyl ($C_1$-$C_4$), and $R_s$ is selected from alkyl, alkenyl, alkynyl, cycloalkyl, aryl, aralkyl, heterocyclylalkyl, or heteroarylalkyl);
  3) $NR_jYR_u$ (wherein $R_j$ is the same as defined above and Y is —$C(=O)$, —$C(=S)$ or $SO_2$ and $R_u$ is selected from alkyl, alkenyl, alkynyl, cycloalkyl, aryl, aralkyl, heteroaryl, heterocyclyl, heteroarylalkyl, and heterocyclylalkyl; and when n is 0 then Y cannot be —$C(=O)$);
  4) —$NR_jC(=T)NR_tR_x$ (wherein $R_t$ is OH or $R_x$ and T is O, S, —$N(CN)$, —$N(NO_2)$, —$CH(NO_2)$, $R_j$ is the same as defined above and $R_x$ is selected from hydrogen, alkyl, alkenyl, alkynyl, cycloalkyl, aryl, aralkyl, heteroaryl, heterocyclyl, heteroarylalkyl, heterocyclylalkyl, and —$S(O)_2R_7$ wherein $R_7$ is the same as defined above);
  5) heterocyclyl;
  6) heteroaryl; and
  7) —$(C=O)NR_aR_b$ (wherein $R_a$ and $R_b$ are independently selected from hydrogen, and $R_u$ wherein $R_u$ is same as defined earlier, also, $R_a$ and $R_b$ together with the nitrogen atom carrying them can be the N-terminus of an amino acid or di-tetrapeptide or $R_a$ and $R_b$ may together join to form a heterocyclyl ring).

$R_3$ can also be

B) —$NR_jR_m$ (wherein $R_j$ is the same as defined above and $R_m$ is selected from alkyl, cycloalkyl, aryl, aralkyl, heteroaryl, heterocyclyl, heteroarylalkyl, and heterocyclylalkyl);

C) —$O(CH_2)_wG_1$ [wherein w is an integer from 1-5 (and $G_1$ is selected from $OR_e$ (wherein Re is the same as defined above), —$NR_jC(=O)OR_s$ (wherein $R_j$ and $R_s$ are the same as defined above), —$NR_jC(=T)NR_tR_x$ (wherein $R_j$, T, $R_t$ and $R_x$ are the same as defined above), —$NR_jYR_u$ (wherein Y, $R_u$ and $R_j$ are the same as defined above), heterocyclyl, and heteroaryl)];

D) —$NR_j(CH_2)_wG_1$ (wherein w, $R_j$ and $G_1$ are the same as defined above);

E) —$O(CH_2)_wG_2$ [wherein w is the same as defined above (and $G_2$ is selected from —$C(=O)NR_aR_b$ (wherein $R_a$ and $R_b$ are the same as defined above), and —$C(=O)OR_k$ (wherein $R_k$ is H or $R_6$ and $R_6$ is the same as defined above); or F) —$NR_j(CH_2)_wG_2$ (wherein w is as defined above, $R_j$ and $G_2$ are the same as defined above))].

Also, when $R_3$ is $OR_e$ then $R_2$ and $R_e$ may together join to form a five membered acetal wherein the carbon linking the two oxygens is substituted with $R_L$ and $R_m$ (wherein $R_L$ and $R_m$ are the same as defined earlier) (and $R_1$ is independently selected from
  a) —$(CH_2)_tG_1$ (wherein t is an integer from 2-4 and $G_1$ are the same as defined above and also when $G_1$ is heterocyclylalkyl group then the said group cannot be 4-(1-pyrrolidinyl) butyl),
  b) —$(CH_2)_wG_2$ (wherein w and $G_2$ are the same as defined above),
  c) aryl,
  d) aralkyl (with the proviso that aralkyl cannot be phenylpropyl),
  e) heteroaryl, and
  f) heterocyclyl (wherein the heteroaryl and heterocyclyl rings are not linked through a heteroatom), and cycloalkyl (with the proviso that cycloalkyl cannot be cyclooctyl).

$R_4$ and $R_5$ can independently be selected from hydrogen, lower ($C_1$-$C_6$) alkyl, lower ($C_2$-$C_6$) alkenyl, lower ($C_2$-$C_6$) alkynyl, lower ($C_3$-$C_8$) cycloalkyl, aryl, acyl, heterocyclyl, heteroaryl, lower ($C_1$-$C_4$) heterocyclylalkyl, and lower ($C_1$-$C_4$) heteroarylalkyl; or $R_4$ and $R_5$ may together form a five-membered acetal wherein the carbon linking the two oxygens is substituted with $R_L$ and $R_m$ (wherein $R_L$ and $R_m$ are the same as defined earlier) with the proviso that when $R_3$ is $OR_e$ then the acetal must be isopropylidene acetal.

The following definitions apply to terms as used herein.

The term "alkyl," unless otherwise specified, refers to a monoradical branched or unbranched saturated hydrocarbon chain having from 1 to 20 carbon atoms. Alkyl groups can be optionally interrupted by atom(s) or group(s) independently selected from oxygen, sulfur, a phenylene, sulphinyl, sulphonyl group or —$NR_\alpha$—, wherein $R_\alpha$ can be hydrogen, alkyl, cycloalkyl, alkenyl, cycloalkenyl, alkynyl, aryl, acyl, aralkyl, —C(=O)OR$_\lambda$, SO$_m$R$_\psi$, or —C(=O)NR$_\lambda$R$_\pi$. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, aryl, heterocyclyl, heteroaryl, (heterocyclyl)alkyl, cycloalkoxy, —CH=N—O (C$_{1-6}$alkyl), —CH=N—NH(C$_{1-6}$alkyl), —CH=N—NH (C$_{1-6}$alkyl)-C$_{1-6}$alkyl, arylthio, thiol, alkylthio, aryloxy, nitro, aminosulfonyl, aminocarbonylamino, —NHC(=O)R$_\lambda$, —NR$_\lambda$R$_\pi$, —C(=O)NR$_\lambda$R$_\pi$, —NHC(=O)NR$_\lambda$R$_\pi$, —C(=O)heteroaryl, C(=O)heterocyclyl, —O—C(=O)NR$_\lambda$R$_\pi$ {wherein R$_\lambda$ and R$_\pi$ are independently selected from hydrogen, halogen, hydroxy, alkyl, alkenyl, alkynyl, alkenyl, alkoxy, cycloalkyl, cycloalkenyl, aryl, aralkyl, heterocyclyl, heteroaryl, heterocyclylalkyl, heteroarylalkyl or carboxy}, nitro or —SO$_m$R$_\psi$ (wherein m is an integer from 0-2 and R$_\psi$ is hydrogen, alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, alkenyl, alkynyl, carboxy, —NR$_\lambda$R$_\pi$, —C(=O)NR$_\lambda$R$_\pi$, —OC(=O)NR$_\lambda$R$_\pi$, —NHC(=O)NR$_\lambda$R$_\pi$, hydroxy, alkoxy, halogen, CF$_3$, cyano, and —SO$_m$R$_\psi$; or an alkyl group also may be interrupted by 1-5 atoms of groups independently selected from oxygen, sulfur or —NR$_\alpha$— (wherein R$_\alpha$, R$_\lambda$, R$_\pi$, m and R$_\psi$ are the same as defined earlier). Unless otherwise constrained by the definition, all substituents may be substituted further by 1-3 substituents selected from alkyl, alkenyl, alkynyl, carboxy, carboxyalkyl, —NR$_\lambda$R$_\pi$, —C(=O)NR$_\lambda$R$_\pi$, —O—C(=O)NR$_\lambda$R$_\pi$, hydroxy, alkoxy, halogen, CF$_3$, cyano, and —SO$_m$R$_\psi$ (wherein R$_\lambda$, R$_\pi$, m and R$_\psi$ are the same as defined earlier); or an alkyl group as defined above that has both substituents as defined above and is also interrupted by 1-5 atoms or groups as defined above.

The term "alkylene," as used herein, refers to a diradical branched or unbranched saturated hydrocarbon chain having from 1 to 6 carbon atoms and one or more hydrogen can optionally be substituted with alkyl, hydroxy, halogen or oximes. This term can be exemplified by groups such as methylene, ethylene, propylene isomers (e.g., —CH$_2$CH$_2$CH$_2$ and —CH(CH$_3$)CH$_2$) and the like. Alkylene may further be substituted with one or more substituents such as alkyl, alkenyl, alkynyl, alkoxy, cycloalkyl, acyl, acylamino, acyloxy, alkoxycarbonylamino, azido, cyano, halogen, hydroxy, oxo, thiocarbonyl, carboxy, arylthio, thiol, alkylthio, aryloxy, heteroaryloxy, aminosulfonyl, —COOR$_\psi$, —NHC(=O)R)$_\lambda$, —NR$_{80}$R$_\pi$, —C(=O)NR$_\lambda$R$_\pi$, —NHC(=O)NR$_\lambda$R$_\pi$, —C(=O)heteroaryl, C(=O)heterocyclyl, —O—C(=O)NR$_\lambda$R$_\pi$, nitro, —S(O)$_m$R$_\lambda$ (wherein R$_\lambda$, R$_\pi$, m and R$_\psi$ are the same as defined earlier). Unless otherwise constrained by the definition, all substituents may be further substituted by 1-3 substituents chosen from alkyl, alkenyl, alkynyl, carboxy, —COOR$_\psi$, —NR$_\lambda$R$_\pi$, —C(=O)NR$_\lambda$)R$_\pi$, —OC(=O)NR$_\lambda$R$_\pi$, —NHC(=O)NR$_\lambda$R$_\pi$, hydroxy, alkoxy, halogen, CF$_3$, cyano, and —S(O)$_m$R$_\psi$ (wherein R$_\lambda$, R$_\pi$, m and R$_\psi$ are the same as defined earlier). Alkylene can also be optionally interrupted by 1-5 atoms of groups independently chosen from oxygen, sulfur and —NR$_\alpha$ (wherein R$_\alpha$ is the same as defined earlier). Unless otherwise constrained by the definition, all may be further substituted by 1-3 substituents selected from hydrogen, alkyl, cycloalkyl, alkenyl, alkynyl, aryl, acyl, aralkyl, alkoxy, hydroxy, carboxy, —C(=O)OR$_\psi$, halogen, CF$_3$, cyano, —NR$_\lambda$R$_\pi$, —S(O)$_m$R$_\psi$, —C(=O)NR$_\lambda$R$_\pi$, —OC(=O)NR$_\lambda$R$_\pi$, —CONH—, —C=O or —C=NOH (wherein R$_\lambda$, R$_\pi$, m and R$_\psi$ are the same as defined earlier).

The term "alkenyl," unless otherwise specified, refers to a monoradical of a branched or unbranched unsaturated hydrocarbon group having from 2 to 20 carbon atoms with cis, trans or geminal geometry. Alkenyl groups can be optionally interrupted by atom(s) or group(s) independently chosen from oxygen, sulfur, phenylene, sulphinyl, sulphonyl and —NR$_\alpha$— (wherein R$_\alpha$ is the same as defined earlier). In the event that alkenyl is attached to a heteroatom, the double bond cannot be alpha to the heteroatom. Alkenyl groups may be substituted further with one or more substituents selected from alkyl, alkenyl, alkynyl, alkoxy, cycloalkyl, cycloalkenyl, acyl, acylamino, acyloxy, —NHC(=O)R$_\lambda$, —NR$_\lambda$R$_\pi$, —C(=O)NR$_\lambda$R$_\pi$—NHC(=O)NR$_{\lambda NR\pi}$, —O—C(=O)NR$_\lambda$R$_\pi$, alkoxycarbonylamino, azido, cyano, halogen, hydroxy, oxo, keto, carboxyalkyl, thiocarbonyl, carboxy, arylthio, thiol, alkylthio, aryl, aralkyl, aryloxy, heterocyclyl, heteroaryl, heterocyclyl alkyl, heteroaryl alkyl, aminosulfonyl, aminocarbonylamino, alkoxyamino, hydroxyamino, alkoxyamino, nitro or SO$_m$R$_\psi$ (wherein R$_\lambda$, R$_\pi$, m and R$_\psi$ are as defined earlier). Unless otherwise constrained by the definition, alkenyl substituents optionally may be substituted further by 1-3 substituents selected from alkyl, alkenyl, alkynyl, carboxy, hydroxy, alkoxy, halogen, —CF$_3$, cyano, —NR$_\lambda$R$_\psi$, —C(=O)NR$_\lambda$R$_\pi$, —O—C(=O)NR$_\lambda$R$_\pi$, and —SO$_m$R$_\psi$ (wherein R$_\lambda$, R$_\pi$, m and R$_\psi$ are as defined earlier). Groups, such as ethenyl or vinyl (CH=CH$_2$), 1-propylene or allyl (—CH$_2$CH=CH$_2$), iso-propylene (—C(CH$_3$)=CH$_2$), bicyclo[2.2.1]heptene, and the like, exemplify this term.

The term "alkenylene" unless otherwise specified, refers to a diradical of a branched or unbranched unsaturated hydrocarbon group preferably having from 2 to 6 carbon atoms with cis, trans or geminal geometry. In the event that alkenylene is attached to the heteroatom, the double bond cannot be alpha to the heteroatom. The alkenylene group can be connected by two bonds to the rest of the structure of compound of Formula I. Alkenylene may further be substituted with one or more substituents such as alkyl, alkenyl, alkynyl, alkoxy, cycloalkyl, acyl, acylamino, acyloxy, —NHC(=O)R$_\lambda$, —NR$_\lambda$R$_\pi$, —C(=O)NR$_\lambda$R$_\pi$, —NHC(=O)NR$_\lambda$R$_\pi$, —OC (=O)NR$_\lambda$R$_\pi$ (wherein R$_\lambda$ and R$_\pi$ are the same as defined earlier), alkoxycarbonylamino, azido, cyano, halogen, hydroxy, oxo, thiocarbonyl, carboxy, —COOR$_\psi$ (wherein R$_\psi$ is the same as defined earlier), arylthio, thiol, alkylthio, aryl, aralkyl, aryloxy, heterocyclyl, heteroaryl, heterocyclyl alkyl, heteroaryl alkyl, aminosulfonyl, alkoxyamino, nitro, —S(O)$_m$R$_\psi$ (wherein R$_\psi$ and m are the same as defined earlier). Unless otherwise constrained by the definition, all substituents may optionally be further substituted by 1-3 substituents chosen from alkyl, alkenyl, alkynyl, carboxy, —COOR$_\psi$ (wherein R$_\psi$ is the same as defined earlier), hydroxy, alkoxy, halogen, —CF$_3$, cyano, —NR$_\lambda$R$_\psi$, —C(=O)NR$_\lambda$R$_\psi$, —OC(=O)NR$_\lambda$R$_\psi$ (wherein R$_\lambda$ and R$_\pi$ are the same as defined earlier) and —S(O)$_m$R$_\psi$ (wherein R$_\psi$ and m are the same as defined earlier).

The term "alkynyl," unless otherwise specified, refers to a monoradical of an unsaturated hydrocarbon, having from 2 to 20 carbon atoms. Alkynyl groups can be optionally interrupted by atom(s) or group(s) independently chosen from oxygen, sulfur, phenylene, sulphinyl, sulphonyl and —NR$_\alpha$— (wherein R$_\alpha$ is the same as defined earlier). In the event that alkynyl groups are attached to a heteroatom, the triple bond cannot be alpha to the heteroatom. Alkynyl groups may be substituted further with one or more substituents selected from alkyl, alkenyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, arylthio, thiol, alkylthio, aryl, aralkyl, aryloxy, aminosulfonyl, aminocarbonylamino, hydroxyamino, alkoxyamino, nitro, heterocyclyl, heteroaryl, heterocyclylalkyl, heteroarylalkyl, —NHC(=O)R$_\lambda$, —NR$_\lambda$R$_\pi$, —NHC(=O)NR$_\lambda$R$_\pi$, —C(=O)NR$_\lambda$R$_\pi$, —O—C(=O)NR$_\lambda$R$_\pi$ or —SO$_m$R$_\psi$ (wherein R$_\lambda$, R$_\pi$, m and R$_\psi$ are the same as defined earlier). Unless otherwise constrained by the definition, alkynyl substituents optionally may be substituted further by 1-3 substituents selected from alkyl, alkenyl, alkynyl, carboxy, carboxyalkyl, hydroxy, alkoxy, halogen, CF$_3$, —NR$_\lambda$R$_\pi$, —C(=O)NR$_\lambda$R$_\pi$, —NHC(=O)NR$_\lambda$R$_\pi$, —C(=O)NR$_\lambda$R$_\pi$, cyano or —SO$_m$R$_\psi$ (wherein R$_\lambda$, R$_\pi$, m and R$_\psi$ are the same as defined earlier).

The term "alkynylene" unless otherwise specified, refers to a diradical of a triply-unsaturated hydrocarbon, preferably having from 2 to 6 carbon atoms. In the event that alkynylene is attached to the heteroatom, the triple bond cannot be alpha to the heteroatom. The alkenylene group can be connected by two bonds to the rest of the structure of compound of Formula I. Alkynylene may further be substituted with one or more substituents such as alkyl, alkenyl, alkoxy, cycloalkyl, acyl, acylamino, acyloxy, alkoxycarbonylamino, azido, cyano, halogen, hydroxy, oxo, thiocarbonyl, carboxy, arylthio, thiol, alkylthio, aryl, aralkyl, aryloxy, aminosulfonyl, nitro, heterocyclyl, heteroaryl, heterocyclyl alkyl, heteroarylalkyl, —NHC(=O)R$_\lambda$, —NR$_\lambda$R$_\pi$, —NHC(=O)NR$_\lambda$R$_\pi$, —C(=O)NR$_\lambda$R$_\pi$, —OC(=O)NR$_\lambda$R$_\pi$ (wherein R$_\lambda$ and R$_\pi$ are the same as defined earlier), —S(O)$_m$R$_\psi$ (wherein R$_\psi$ and m are the same as defined earlier). Unless otherwise constrained by the definition, all substituents may optionally be further substituted by 1-3 substituents chosen from alkyl, alkenyl, alkynyl, carboxy, —COOR$_\psi$ (wherein R$_\psi$ is the same as defined earlier), hydroxy, alkoxy, halogen, CF$_3$, —NR$_\lambda$R$_\pi$, —C(=O)NR$_\lambda$R$_\pi$, —NHC(=O)Nr$_\lambda$R$_\pi$, —C(=O)NR$_{80}$R$_\pi$, (wherein R$_\lambda$ and R$_\pi$ are the same as defined earlier), cyano, and —S(O)$_m$R$_\psi$ (wherein R$_\psi$ and m are the same as defined earlier).

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like or multiple ring structures, including adamantanyl, and bicyclo[2.2.1]heptane or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —NR$_\lambda$R$_\pi$, —NHC(=O)NR$_\lambda$R$_\pi$, —NHC(=O)R$_\lambda$, —C(=O)NR$_\lambda$R$_\pi$, —O—C(=O)NR$_\lambda$R$_\pi$, nitro, heterocyclyl, heteroaryl, heterocyclylalkyl, heteroarylalkyl or —SO$_m$R$_\psi$ (wherein R$_\lambda$, R$_\pi$, m and R$_\psi$ are the same as defined earlier). Unless otherwise constrained by the definition, cycloalkyl substituents optionally may be substituted further by 1-3 substituents selected from alkyl, alkenyl, alkynyl, carboxy, hydroxy, alkoxy, halogen, CF$_3$, —NR$_\lambda$R$_\pi$, —C(=O)NR$_\lambda$R$_\pi$, —NHC(=O)NR$_\lambda$R$_\pi$, —OC(=O)NR$_\lambda$R$_\pi$, cyano or —SO$_m$R$_\psi$ (wherein R$_\lambda$, R$_\pi$, m and R$_\psi$ are the same as defined earlier). "Cycloalkylalkyl" refers to alkyl-cycloalkyl group linked through alkyl portion, wherein the alkyl and cycloalkyl are the same as defined earlier.

The term "alkoxy" denotes the group O-alkyl wherein alkyl is the same as defined above.

The term "aralkyl," unless otherwise specified, refers to alkyl-aryl linked through an alkyl portion (wherein alkyl is as defined above) and the alkyl portion contains 1-6 carbon atoms and aryl is as defined below. Examples of aralkyl groups include benzyl, ethylphenyl, propylphenyl, naphthylmethyl and the like.

The term "aryl," unless otherwise specified, refers to aromatic system having 6 to 14 carbon atoms, wherein the ring system can be mono-, bi- or tricyclic and are carbocyclic aromatic groups. For example, aryl groups include, but are not limited to, phenyl, biphenyl, anthryl or naphthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, CF$_3$, cyano, nitro, COOR$_\psi$, NHC(=O)R$_\lambda$, —NR$_\lambda$R$_\pi$, —C(=O)NR$_\lambda$R$_\pi$, —NHC(=O)NR$_\lambda$R$_\pi$, —O—C(=O)NR$_\lambda$R$_\pi$, —SO$_m$R$_\psi$, carboxy, heterocyclyl, heteroaryl, heterocyclylalkyl, heteroarylalkyl or amino carbonyl amino, mercapto, haloalkyl, optionally substituted aryl, optionally substituted heterocyclylalkyl, thioalkyl, —CONHR$_\pi$, —OCOR$_\pi$, —COR$_\pi$, —NHSO$_2$R$_\pi$ or —SO$_2$NHR$_\pi$ (wherein R$_\lambda$, R$_\pi$, m and R$_\psi$ are the same as defined earlier). Aryl groups optionally may be fused with a cycloalkyl group, wherein the cycloalkyl group may optionally contain heteroatoms selected from O, N or S. Groups such as phenyl, naphthyl, anthryl, biphenyl, and the like exemplify this term.

The term "aryloxy" denotes the group O-aryl wherein aryl is the same as defined above.

The term "carboxy" as defined herein refers to —C(=O)OH.

The term "heteroaryl," unless otherwise specified, refers to an aromatic ring structure containing 5 or 6 ring atoms or a bicyclic or tricyclic aromatic group having from 8 to 10 ring atoms, with one or more heteroatom(s) independently selected from N, O or S optionally substituted with 1 to 4 substituent(s) selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —NR$_\lambda$R$_\pi$, CH=NOH, —(CH$_2$)$_w$C(=O)R$_\eta$ {wherein w is an integer from 0-4 and R$_\eta$ is hydrogen, hydroxy, OR$_\lambda$, NR$_\lambda$R$_\pi$, —NHOR$_\omega$ or —NHOH}, —C(=O)NR$_\lambda$R$_\pi$ —NHC(=O)NR$_\lambda$R$_\pi$, —SO$_m$R$_\psi$, —O—C(=O)NR$_\lambda$R$_\pi$, —O—C(=O)R$_\lambda$), or —O—C(=O)OR$_\lambda$ (wherein m, R$_\psi$, R$_\lambda$ and R$_\pi$ are as defined earlier and R$_\omega$ is alkyl, cycloalkyl, aryl, heteroaryl, heterocyclyl, heteroarylalkyl or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzthiazinyl, benzthiazinonyl, benzoxazinyl, benzoxazinonyl, quinazonyl, carbazolyl phenothiazinyl, phenoxazinyl, benzothiazolyl or benzoxazolyl, and the like.

The term "heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, acyl, optionally substituted aryl, alkoxy, alkaryl, cyano, nitro, oxo, carboxy, optionally substituted heterocyclyl, optionally substituted heterocyclylalkyl, optionally substituted heteroaryl, —O—C(=O)R$_\lambda$, —O—C(=O)OR$_\lambda$, —C(=O)NR$_\lambda$R$_\pi$, SO$_m$R$_\psi$, —O—C(=O)NR$_\lambda$R$_\pi$, —NHC(=O)NR$_\lambda$R$_\pi$, —NR$_\lambda$R$_\pi$, mercapto, haloalkyl, thioalkyl, —COOR$_\psi$, —COONHR$_\lambda$, —COR$_\lambda$, —NHSO$_2$R$_\lambda$ or SO$_2$NHR$_\lambda$ (wherein m, R$_\psi$, R$_\lambda$ and R$_\pi$ are as defined earlier) or guanidine. Heterocyclyl can optionally include rings having one or more double bonds. Such ring systems can be mono-, bi- or tricyclic. Carbonyl or sulfonyl group can replace carbon atom(s) of heterocyclyl. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include oxazolidinyl, tetrahydrofuranyl, dihydrofuranyl, benzoxazinyl, benzthiazinyl, imidazolyl, benzimidazolyl, tetrazolyl, carbaxolyl, indolyl, phenoxazinyl, phenothiazinyl, dihydropyridinyl, dihydroisoxazolyl, dihydrobenzofuryl, azabicyclohexyl, thiazolidinyl, dihydroindolyl, pyridinyl, isoindole 1,3-dione, piperidinyl, tetrahydropyranyl, piperazinyl, 3H-imidazo[4,5-b]pyridine, isoquinolinyl, 1H-pyrrolo[2,3-b]pyridine or piperazinyl and the like.

"Heteroarylalkyl" refers to alkyl-heteroaryl group linked through alkyl portion, wherein the alkyl and heteroaryl are the same as defined earlier.

"Heterocyclylalkyl" refers to alkyl-heterocyclyl group linked through alkyl portion, wherein the alkyl and heterocyclyl are the same as defined earlier.

"Acyl" refers to —C(=O)R" wherein R" is selected from the group alkyl, cycloalkyl, aryl, aralkyl, heteroaryl, heterocyclyl, heteroarylalkyl or heterocyclylalkyl.

"Substituted amino" unless otherwise specified, refers to a group —N(R$_k$)$_2$ wherein each R$_k$ is independently selected from the group hydrogen provided that both R$_k$ groups are not hydrogen (defined as "amino"), alkyl, alkenyl, alkynyl, aralkyl, cycloalkyl, aryl, heteroaryl, heterocyclyl, heterocyclylalkyl, heteroarylalkyl, acyl, S(O)$_m$R$_\psi$ (wherein m and R$_\psi$ are the same as defined above), —C(=R$_v$)NR$_\lambda$R$_y$ (wherein R$_v$ is O or S & R$_\lambda$ and R$_y$ are the same as defined earlier) or NHC(=R$_v$)NR$_y$R$_\lambda$ (wherein R$_v$, R$_y$ and R$_\lambda$ are the same as defined earlier). Unless otherwise constrained by the definition, all amino substituents may optionally be further substituted by 1-3 substituents chosen from alkyl, aralkyl, cycloalkyl, aryl, heteroaryl, heterocyclyl, carboxy, —COOR$_\psi$ (wherein R$_\psi$ is the same as defined earlier), hydroxy, alkoxy, halogen, CF$_3$, cyano, —C(=R$_v$)NR$_\lambda$R$_y$ (wherein R$_v$ is the same as defined earlier), —O(C=O)NR$_\lambda$R$_y$, —OC(=R$_v$)NR$_\lambda$R$_y$ (wherein R$_\lambda$, R$_y$ and R$_v$ are the same as defined earlier), —S(O)$_m$R$_\psi$ (wherein R$_\psi$ and m are the same as defined above).

The term "leaving group" generally refers to groups that exhibit the properties of being labile under the defined synthetic conditions and also, of being easily separated from synthetic products under defined conditions. Examples of such leaving groups include, but are not limited to, halogen (F, Cl, Br, I), triflates, tosylates, mesylates, alkoxy, thioalkoxy, hydroxy radicals and the like.

The term "activated derivative of a carboxylic acid," can include, for example, protected amino acids, aliphatic acids or aromatic acids converted to their corresponding acyl halides (e.g., acid fluoride, acid chloride and acid bromide), corresponding activated esters (e.g., nitro phenyl ester, the ester of 1-hydroxybenzotriazole or the ester of hydroxysuccinimide, HOSu) or mixed anhydrides, for example, anhydride with ethyl chloroformate and other derivatives within the skill of the art.

The term "protecting groups" is used herein to refer to moieties which have the property of preventing specific chemical reaction at a site on the molecule undergoing chemical modification intended to be left unaffected by the particular chemical modification. Also the term protecting group, unless otherwise specified, may be used with groups such as hydroxy, amino and carboxy. Examples of such groups are found in T. W. Greene and P. G. M. Wuts, "Protective Groups in Organic Synthesis", 2$^{nd}$ Ed., John Wiley and Sons, New York, N.Y. The species of the carboxylic protecting groups, amino protecting groups or hydroxy protecting group employed are not critical, so long as the derivatised moieties/moiety is/are stable to conditions of subsequent reactions and can be removed without disrupting the remainder of the molecule. "Amino acid" refers to both natural and unnatural amino acids. The term "natural amino acid," as used hereind, is intended to represent the twenty two naturally-occurring amino acids glycine, alanine, valine, leucine, isoleucine, serine, methionine, threonine, phenylalanine, tyrosine, trytophan, cysteine, proline, histidine, aspartic acid, asparagines, glutamic acid, glutamine, γ-carboxyglutamic acid, arginine, ornithine and lysine in their L form. The term "unnatural amino acid," as used herein, is intended to represent the 'D' form of the twenty two naturally-occurring amino acids described above. It is further understood that the term unnatural amino acid includes homologues of the natural amino acids, and synthetically modified form of the natural amino acids commonly utilized by those in the peptide chemistry arts when preparing synthetic analogues of naturally occurring peptides, including D and L forms. The synthetically modified forms include amino acids having alkylene chains shortened or lengthened by up to two carbon atoms, amino acids comprising optionally substituted aryl groups, and amino acids comprised halogenated groups preferably halogenated alkyl and aryl groups. The term "unnatural amino acids" as used herein is also intended to represent beta amino acids.

The term "peptide" refers to a molecule comprising amino acids linked through amide linkages. Dipeptide comprises of 2 amino acids, tripeptide refers to a peptide having 3 amino acids and tetrapeptide refers to one having four amino acids, wherein the term amino acid is as defined earlier. "LDVP" refers to a tetrapeptide leucyl-aspartyl-valyl-prolyl. "DVP" refers to a tripeptide aspartyl-valyl-prolyl. "VP" refers to a dipeptide valyl-prolyl.

Compounds disclosed herein contain one or more asymmetric carbon atoms and thus can exist as racemates and racemic mixtures, single enantiomers, diastereomeric mixtures and individual diastereomers. All such isomeric forms of these compounds are expressly included herein. Each stereogenic carbon may be of the R or S configuration. Although the specific compounds exemplified in this application may be depicted in a particular stereochemical configuration, compounds having either the opposite stereochemistry at any given chiral center or mixtures thereof are envisioned. Although amino acids and amino acid side chains may be depicted in a particular configuration, both natural and unnatural forms are envisioned.

DETAILED DESCRIPTION OF THE INVENTION

Compounds disclosed herein may be prepared by techniques well known in the art and familiar to a practitioner of ordinary skill in art. In addition, compounds disclosed herein may be prepared by the processes described herein, although these processes are not the only means by which the compounds described may be synthesised. Further, particular synthetic steps described herein may be performed in an alternate sequence or order to give the desired compounds.

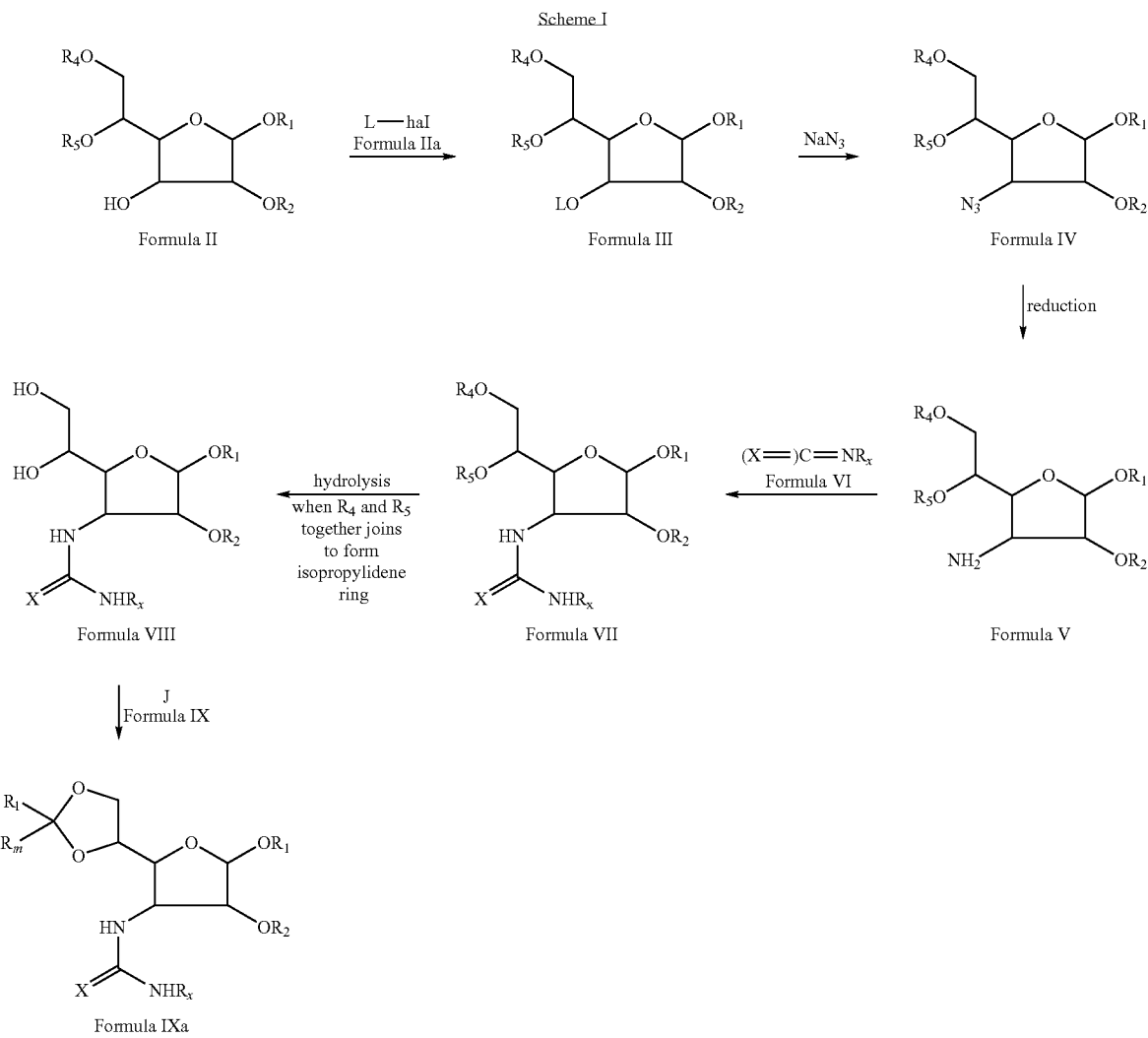

Scheme I

Compounds of Formula VIII can be prepared, for example, by Scheme I. Thus, a compound of Formula II (wherein $R_1$, $R_2$, $R_4$ and $R_5$ are the same as defined earlier) can be reacted with a compound of Formula IIa [wherein L is a leaving group such as tosyl or mesyl and hal is a halogen (Cl, Br, I)] to give a compound of Formula III, which can be reacted with sodium azide to form a compound of Formula IV, which can undergo reduction to form a compound of Formula V, which can be reacted with a compound of Formula VI (wherein X is O or S and $R_x$ the same as defined earlier) to furnish a compound of Formula VII, which can undergo hydrolysis to give a compound of Formula VIII, which can be reacted with a compound of Formula IX (wherein J is

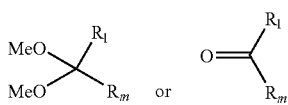

wherein $R_1$ and $R_m$ are the same as defined earlier) to form a compound of Formula IXa.

The reaction of a compound of Formula II with a compound of Formula IIa to form a compound of Formula III can be carried out in the presence of an organic base, such as, for example, pyridine, triethylamine or diisopropylethylamine. Alternatively, the hydroxyl group in a compound of Formula II can also be converted to a triflyl group with, for example, triflic anhydride.

The reaction of a compound of Formula III with sodium azide to give a compound of Formula IV can be carried out in an organic solvent such as, for example, dimethylformamide, dimethylsulphoxide, tetrahydrofuran, dioxane or diethyl ether. Alternatively, one may also use, for example, trimethylsilyl azide or lithium azide in place of sodium azide.

The reduction of a compound of Formula IV to yield a compound of Formula V can be carried out in an organic solvent such as, for example, tetrahydrofuran, dimethylformamide, diethylether or dioxane, with a reducing agent such as, for example, lithium aluminium hydride or sodium borohydride.

The reaction of a compound of Formula V with an isocyanate or isothiocyanate of Formula VI to yield a compound of Formula VII can be carried out in an organic solvent such as, for example, acetonitrile, dichloromethane, dichloroethane, chloroform or carbon tetrachloride.

Alternatively, a compound of Formula VII can also be prepared by reacting a compound of Formula V with an appropriate amine in the presence of reagents such as, for example, carbonyldiimidazole (CDI) or with carbamates such as, for example, phenyl carbamate or p-nitrophenyl carbamate of an amine. Also, optionally thiocarbonyldiimidazole or an isothiocyanate, for example, can be used in place of carbonyldiimidazole or isocyanate, respectively in the reaction.

A compound of Formula VII can be hydrolysed (when $R_4$ and $R_5$ together join to form isopropylidene ring) to give a compound of Formula VIII with the reagents, for example, aqueous perchloric acid, aqueous acetic acid, aqueous sulphuric acid or Dowex 50W-8X (commercially available) in an organic solvent such as, for example, methanol, ethanol, tetrahydrofuran, dimethylformamide, dioxane or diethyl ether.

The reaction of a compound of Formula VIII with a compound of Formula IX (when J is

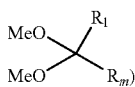

to give a compound of Formula IXa can be carried out in an organic solvent, for example, toluene, dimethylformamide, benzene, xylene or hexane in the presence of catalyst, for example, para-toluene sulphonic acid, cupric chloride dihydrate, cuprous chloride, cuprous bromide, cupric fluoride dihydrate, cupric sulphate pentahydrate, cupric pyrophosphate trihydrate, cupric formate tetrahydrate, cuprous cyanide, cupric oxide, cupric hydroxide, cuprous oxide, cupric acetate or copper powder.

The reaction of a compound of Formula VIII with a compound of Formula IX (when J is

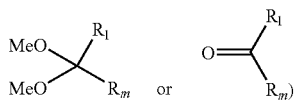

to give a compound of Formula IXa can be carried out in an organic solvent, for example, dichloromethane, chloroform, carbon tetrachloride, dichloroethane or toluene in the presence of catalyst, for example, para-toluenesulphonic acid, cupric chloride dihydrate, cuprous chloride, cuprous bromide, cupric fluoride dihydrate, cupric sulphate pentahydrate, cupric oxide, cupric hydroxide, cuprous oxide, cupric acetate or copper powder and molecular sieves.

Particular illustrative compounds include those described below, for example, 1,2-O-isopropylidene-3-deoxy-3-(phenyl-thiourido)-α-D-glucofuranoside (Compound No. 1), 1,2-O-isopropylidene-3-deoxy-3-[(trifluoromethylphenyl)-thiourido]α-D-glucofuranoside (Compound No. 2), 1,2-O-isopropylidene-3-deoxy-3-[(4-fluorophenyl)-thiourido]-α-D-glucofuranoside (Compound No. 3), 1,2-O-isopropylidene-3-deoxy-3-[(4-methoxyphenyl)-thiourido]-α-D-glucofuranoside (Compound No. 4), 1,2-O-isopropylidene-3-deoxy-3-[(2,6-dimethylphenyl)-thiourido]-α-D-glucofuranoside (Compound No. 5), 1,2-O-isopropylidene-3-deoxy-3-[(2,4-dichlorophenyl)-thiourido]-α-D-glucofuranoside (Compound No. 6), 1,2-O-isopropylidene-3-deoxy-3-[(2,4-difluorophenyl)-thiourido]-α-D-glucofuranoside (Compound No. 7), 1,2-O-isopropylidene-3-deoxy-3-[(3-nitrophenyl)-thiourido]-5,6-dioxa spiro[4,5]decane-α-D-glucofuranoside (Compound No. 8), 1,2-O-isopropylidene-3-deoxy-3-[(4-nitrophenyl)-thiourido]-α-D-glucofuranoside (Compound No. 9), 1,2-O-isopropylidene-3-deoxy-3-[(2-nitrophenyl)-thiourido]-α-D-glucofuranoside (Compound No. 10), 1,2-O-isopropylidene-3-deoxy-3-{[4-(4-cyclohexylpropyl)phenyl]-thiourido}-α-D-glucofuranoside (Compound No. 11), 1,2-O-isopropylidene-3-deoxy-3-[(3-nitrophenyl)-thiourido]-α-D-glucofuranoside (Compound No. 12), 1,2-O-isopropylidene-3-deoxy-3-[(4-fluorophenyl)-thiourido]-5,6-dioxa spiro[4,5]decane-α-D-glucofuranoside (Compound No. 48), 1,2-O-isopropylidene-3-deoxy-3-[(2-fluorophenyl)-thiourido]-5,6-dioxa spiro[4,5]decane-α-D-glucofuranoside (Compound No. 49), 1,2-O-isopropylidene-3-deoxy-3-[(2-nitrophenyl)-thiourido]-5,6-dioxa spiro[4,5]decane-α-D-glucofuranoside (Compound No. 50), 1,2-O-isopropylidene-3-deoxy-3-[(2,6-dimethylphenyl)-thiourido]-5,6-dioxa spiro[4,5]decane-α-D-glucofuranoside (Compound No. 51), 1,2-O-isopropylidene-3-deoxy-3-(phenyl-thiourido)-5,6-dioxa spiro[4,5]decane-α-D-glucofuranoside (Compound No. 52), 1,2-O-isopropylidene-3-deoxy-3-[(2-methoxyphenyl)-thiourido]-5,6-dioxa spiro[4,5]decane-α-D-glucofuranoside (Compound No. 53), 1,2-O-isopropylidene-3-deoxy-3-[(2,4-difluorophenyl)-thiourido]-5,6-dioxa spiro[4,5]decane-α-D-glucofuranoside (Compound No. 54), 1,2-O-isopropylidene-3-deoxy-3-[(4-nitrophenyl)-thiourido]-5,6-dioxa spiro[4,5]decane-α-D-glucofuranoside (Compound No. 55), 1,2-O-isopropylidene-3-deoxy-3-[(2,4-dichlorophenyl)-thiourido]-5,6-dioxa spiro[4,5]decane-α-D-glucofuranoside (Compound No. 56), 1,2-O-isopropylidene-3-deoxy-3-[(4-cyanophenyl)-thiourido]-5,6-dioxa spiro[4,5]decane-α-D-glucofuranoside (Compound No. 61), 1,2-O-isopropylidene-3-deoxy-3-{[4-(4-cyclohexylpropyl)phenyl]-thiourido}-5,6-dioxa spiro[4,5]decane-α-D-glucofuranoside (Compound No. 62), 1,2-O-isopropylidene-3-deoxy-3-[(3-methoxyphenyl)-thiourido]-α-D-glucofuranoside (Compound No. 63), 1,2-O-isopropylidene-3-deoxy-3-[(2-fluorophenyl)-thiourido]-α-D-glucofuranoside (Compound No. 64), 1,2-O-isopropylidene-3-deoxy-3-[(4-cyanophenyl)-thiourido]-α-D-glucofuranoside (Compound No. 65), 1,2-O-isopropylidene-3-deoxy-3-[(4-trifluoromethylphenyl)-thiourido]-5,6-dioxa spiro[4,5]decane-α-D-glucofuranoside (Compound No. 66), and their pharmaceutically acceptable salts, pharmaceutically acceptable solvates, esters, enantiomers, diastereomers, N-oxides, polymorphs, metabolites.

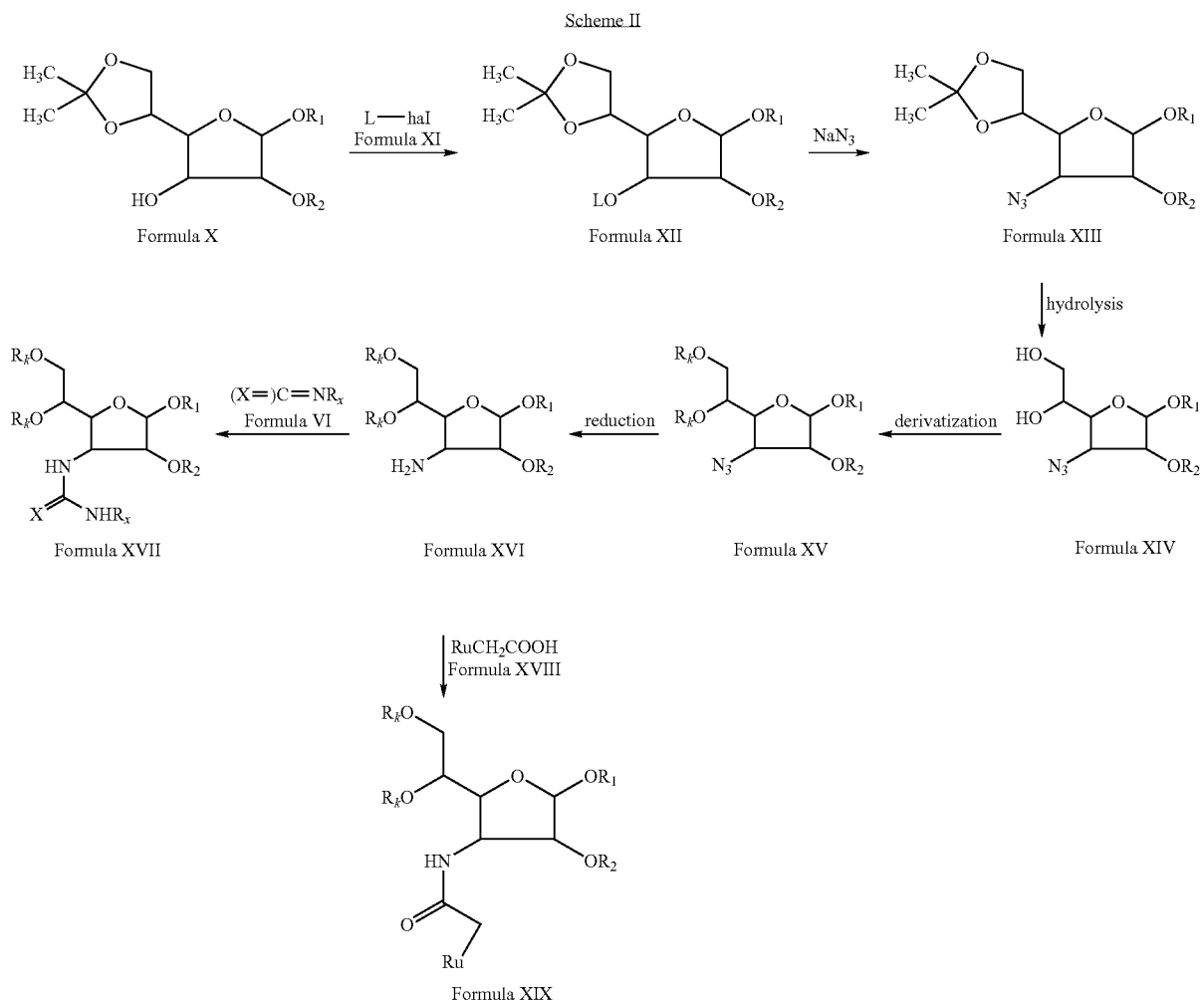

Scheme II

The compounds of Formula XVII can be prepared, for example, following a procedure as depicted in Scheme II, for example. Thus the compound of Formula X (wherein $R_1$ and $R_2$ are the same as defined earlier) can be reacted with a compound of Formula XI (wherein L is is the same as defined earlier) to form a compound of Formula XII, which can be reacted with sodium azide to form a compound of Formula XIII, which can undergo hydrolysis to give a compound of Formula XIV, which can be derivatized to give a compound of Formula XV, which can be reduced to give a compound of Formula XVI, which can be reacted with a compound of Formula VI (wherein X is O or S and $R_x$ is the same as defined earlier) to furnish a compound of Formula XVII. A compound of Formula XVI can be reacted with a compound of Formula XVIII to give a compound of Formula XIX.

A compound of Formula X can be reacted with a compound of Formula XI to form a compound of Formula XII in the presence of an organic base, such as, for example, pyridine, triethylamine or diisopropylethylamine. Alternatively, the hydroxyl group in a compound of Formula X can also be converted to a triflyl group with, for example, triflic anhydride.

A compound of Formula XII can be reacted with sodium azide to give a compound of Formula XIII in an organic solvent such as, for example, dimethylformamide, dimethyl- sulphoxide, tetrahydrofuran, dioxane or diethyl ether. Alternatively, one may also use, for example, trimethylsilyl azide or lithium azide in place of sodium azide.

A compound of Formula XIII can be hydrolyzed to give a compound of Formula XIV with the reagents, for example, aqueous perchloric acid, aqueous acetic acid, aqueous sulphuric acid or Dowex 50W-8X (commercially available) in an organic solvent such as, for example, methanol, ethanol, tetrahydrofuran, dimethylformamide, dioxane or diethyl ether.

A compound of Formula XIV can be derivatised to give a compound of Formula XV in an organic solvent, for example, dimethylformamide, dimethylsulphoxide, diethylether, tetrahydrofuran or acetonitrile in the presence of a base, for example, sodium hydride, potassium hydride, sodium tert-butoxide, potassium tert-butoxide or sodium amide.

A compound of Formula XV can be reduced to give a compound of Formula XVI in an organic solvent such as, for example, tetrahydrofuran, dioxane, ethanol or diethyl ether, with a reducing agent such as, for example, lithium aluminum hydride or sodium borohydride.

Alternatively, the reduction of a compound of Formula XV can also be carried out by hydrogenation in the presence of, for example, catalytic palladium on carbon.

A compound of Formula XVI can be reacted with a compound of Formula VI to yield a compound of Formula XVII in an organic solvent such as, for example, acetonitrile, dichloromethane, dichloroethane, chloroform or carbon tetrachloride.

A compound of Formula XVI can be reacted with a compound of Formula XVIII to give a compound of Formula XIX in the presence of coupling agents such as, for example, 1-(3-dimethylaminopropyl)-3-ethyl-carbodimide, N,N'-dicyclohexylcarbodiimide, 2-(1-H-benzotriazol-1-yl)-1,1,3,3-tetramethyluronium hexafluorophosphate (HBTU), O-(7-azabenzotriazol-1-yl)-N,N,N',N'-tetramethyluronium hexafluorophosphate (HATU), (benzotriazol-1-yloxy)tris-(dimethylamino)phosphonium hexafluorophosphate (BOP), propane phosphonic acid anhydride (T3P), O-(benzotriazol-1-yl)-N,N,N',N'-tetramethyluronium tetrafluoroborate (TBTU), S-(1-oxido-2-pyridinyl)-1,1,3,3-tetramethylthiouronium tetrafluoroborate (TOTT), N,N,N',N'-tetramethyl-O-(3,4-dihydro-4-oxo-1,2,3-benzotriazin-3-yl)uronium tetrafluoroborate (TDBTU), O-(1,2-dihydro-2-oxo-pyridyl]-N,N,N',N'-tetramethyluronium tetrafluoroborate (TPTU), O-((ethoxycarbonyl) cyanomethylenamino)-N,N,N',N'-tetramethyluronium tetrafluoroborate (TOTU), chlortripyrrolidino phosphoniumhexafluorophosphate (PyClop), benzotriazol-1-yl-oxy-tris-pyrrolidino-phosphonium hexafluorophosphate (PyBOP), chlorodipyrrolidinocarbenium hexafluorophosphate (PyClU), benzotriazol-1-yloxy) dipiperidinocarbenium hexafluorophosphate (HBPipU) or mixtures thereof in the presence of one or more of additives or activating agents such as, for example, 1-hydroxybenzotriazole, acetone oxime, 2-hydroxypyridine, N-hydroxysuccinimide, pentafluorophenol or mixtures thereof and in the presence of one or more of organic bases, for example, N-methylmorpholine, N-methylmorpholine oxide, N-ethylmorpholine, 1-methylpiperidine, triethylamine, tribenzylamine, piperidine, N-ethyldiisopropylamine, 2,6-lutidine or mixtures thereof, polar aprotic solvents such as dimethylformamide or dimethylsulphoxide, ethers, for example, tetrahydrofuran, dioxane or diethyl ether, halogenated solvents, for example, dichloromethane, dichloroethane, carbon tetrachloride or chloroform or mixtures thereof.

Particular illustrative compounds include those listed below, for example, 1,2-O-isopropylidene-3-deoxy-3-[(4-fluorophenyl)-thiourido]-5,6-di-O-ethyl-α-D-glucofuranoside (Compound No. 13), 1,2-O-isopropylidene-3-deoxy-3-[(2-fluorophenyl)-thiourido]-5,6-di-O-ethyl-α-D-glucofuranoside (Compound No. 14), 1,2-O-isopropylidene-3-deoxy-3-[(2-methoxyphenyl)-thiourido]-5,6-di-O-ethyl-α-D-glucofuranoside (Compound No. 15), 1,2-O-isopropylidene-3-deoxy-3-[(4-cyanophenyl)-thiourido]-5,6-di-O-ethyl-α-D-glucofuranoside (Compound No. 16), 1,2-O-isopropylidene-3-deoxy-3-[(4-trifluoromethylphenyl)-thiourido]-5,6-di-O-ethyl-α-D-glucofuranoside (Compound No. 17), 1,2-O-isopropylidene-3-deoxy-3-[(2-trifluoromethylphenyl)-thiourido]-5,6-di-O-ethyl-α-D-glucofuranoside (Compound No. 18), 1,2-O-isopropylidene-3-deoxy-3-(phenyl-thiourido)-5,6-di-O-ethyl-α-D-glucofuranoside (Compound No. 19), 1,2-O-isopropylidene-3-deoxy-3-[(4-fluorophenyl)-thiourido]-5,6-di-O-propyl-α-D-glucofuranoside (Compound No. 20), 1,2-O-isopropylidene-3-deoxy-3-[(2-fluorophenyl)-thiourido]-5,6-di-O-propyl-α-D-glucofuranoside (Compound No. 21), 1,2-O-isopropylidene-3-deoxy-3-[(2-methoxyphenyl)-thiourido]-5,6-di-O-propyl-α-D-glucofuranoside (Compound No. 22), 1,2-O-isopropylidene-3-deoxy-3-[(4-cyanophenyl)-thiourido]-5,6-di-O-propyl-α-D-glucofuranoside (Compound No. 23), 1,2-O-isopropylidene-3-deoxy-3-[(4-trifluoromethylphenyl)-thiourido]-5,6-di-O-propyl-α-D-glucofuranoside (Compound No. 24), 1,2-O-isopropylidene-3-deoxy-3-[(2-trifluoromethylphenyl)-thiourido]-5,6-di-O-propyl-α-D-glucofuranoside (Compound No. 25), 1,2-O-isopropylidene-3-deoxy-3-(phenyl-thiourido)-5,6-di-O-propyl-α-D-glucofuranoside (Compound No. 26), 1,2-O-isopropylidene-3-deoxy-3-[(4-fluorophenyl)-thiourido]-5,6-di-O-butyl-α-D-glucofuranoside (Compound No. 27), 1,2-O-isopropylidene-3-deoxy-3-[(2-fluorophenyl)-thiourido]-5,6-di-O-butyl-α-D-glucofuranoside (Compound No. 28), 1,2-O-isopropylidene-3-deoxy-3-[(2-methoxyphenyl)-thiourido]-5,6-di-O-butyl-α-D-glucofuranoside (Compound No. 29), 1,2-O-isopropylidene-3-deoxy-3-[(4-cyanophenyl)-thiourido]-5,6-di-O-butyl-α-D-glucofuranoside (Compound No. 30), 1,2-O-isopropylidene-3-deoxy-3-[(4-trifluoromethylphenyl)-thiourido]-5,6-di-O-butyl-α-D-glucofuranoside (Compound No. 31), 1,2-O-isopropylidene-3-deoxy-3-[(2-trifluoromethylphenyl)-thiourido]-5,6-di-O-butyl-α-D-glucofuranoside (Compound No. 32), 1,2-O-isopropylidene-3-deoxy-3-(phenyl-thiourido)-5,6-di-O-butyl-α-D-glucofuranoside (Compound No. 33), 1,2-O-isopropylidene-3-deoxy-3-[(4-fluorophenyl)-thiourido]-5,6-di-O-pentyl-α-D-glucofuranoside (Compound No. 34), 1,2-O-isopropylidene-3-deoxy-3-[(2-fluorophenyl)-thiourido]-5,6-di-O-pentyl-α-D-glucofuranoside (Compound No. 35), 1,2-O-isopropylidene-3-deoxy-3-[(2-methoxyphenyl)-thiourido]-5,6-di-O-pentyl-α-D-glucofuranoside (Compound No. 36), 1,2-O-isopropylidene-3-deoxy-3-[(4-cyanophenyl)-thiourido]-5,6-di-O-pentyl-α-D-glucofuranoside (Compound No. 37), 1,2-O-isopropylidene-3-deoxy-3-[(4-trifluoromethylphenyl)-thiourido]-5,6-di-O-pentyl-α-D-glucofuranoside (Compound No. 38), 1,2-O-isopropylidene-3-deoxy-3-[(2-trifluoromethylphenyl)-thiourido]-5,6-di-O-pentyl-α-D-glucofuranoside (Compound No. 39), 1,2-O-isopropylidene-3-deoxy-3-(phenyl-thiourido)-5,6-di-O-pentyl-α-D-glucofuranoside (Compound No. 40), 1,2-O-isopropylidene-3-deoxy-3-[(4-fluorophenyl)-thiourido]-5,6-di-O-hexyl-α-D-glucofuranoside (Compound No. 41), 1,2-O-isopropylidene-3-deoxy-3-[(2-fluorophenyl)-thiourido]-5,6-di-O-hexyl-α-D-glucofuranoside (Compound No. 42), 1,2-O-isopropylidene-3-deoxy-3-[(2-methoxyphenyl)-thiourido]-5,6-di-O-hexyl-α-D-glucofuranoside (Compound No. 43), 1,2-O-isopropylidene-3-deoxy-3-[(4-cyanophenyl)-thiourido]-5,6-di-O-hexyl-α-D-glucofuranoside (Compound No. 44), 1,2-O-isopropylidene-3-deoxy-3-[(4-trifluoromethylphenyl)-thiourido]-5,6-di-O-hexyl-α-D-glucofuranoside (Compound No. 45), 1,2-O-isopropylidene-3-deoxy-3-[(2-trifluoromethylphenyl)-thiourido]-5,6-di-O-hexyl-α-D-glucofuranoside (Compound No. 46), 1,2-O-isopropylidene-3-deoxy-3-(phenyl-thiourido)-5,6-di-O-hexyl-α-D-glucofuranoside (Compound No. 47), 1,2-O-isopropylidene-3-deoxy-3-[(2-chloro-4-fluorophenyl)-amido]-5,6-di-O-pentyl-α-D-glucofuranoside (Compound No. 57), 1,2-O-isopropylidene-3-deoxy-3-[(2,4-difluorophenyl)-amido]-5,6-di-O-pentyl-α-D-glucofuranoside (Compound No. 58), 1,2-O-isopropylidene-3-deoxy-3-[(2,4-difluorophenyl)-amido]-5,6-di-O-hexyl-α-D-glucofuranoside (Compound No. 59), 1,2-O-isopropylidene-3-deoxy-3-[(2-chloro-4-fluorophenyl)-amido]-5,6-di-O-pentyl-α-D-glucofuranoside (Compound No. 60), and their pharmaceutically acceptable salts, pharmaceutically acceptable solvates, esters, enantiomers, diastereomers, N-oxides, polymorphs, metabolites Also, in all the above representative examples wherever esters are specified, one skilled in the art could optionally hydrolyze them to their respective acids, for example hydrolysis of alkyl esters (such as ethyl, methyl or benzyl ester) to their corresponding acids can be carried out in the presence of a base, for example, lithium hydroxide, sodium hydroxide or potassium hydroxide. Alternatively, hydrolysis of benzyl ester can be carried out hydrogenatically using catalysts, for example, palladium on carbon or platinum on carbon. Esters such as tert-butyl can be hydrolyzed to their corresponding acids in the presence of acid, for example, trifluoroacetic acid or hydrochloric acid.

In the above schemes, where specific bases, acids, solvents, condensing agents, hydrolyzing agents, etc., are mentioned, it is to be understood that other acids, bases, solvents, condensing agents, hydrolyzing agents, etc., may also be used. Similarly, the reaction temperature and duration of the reactions may be adjusted according to the requirements that arise during the process.

Examples set forth general synthetic procedures for the preparation of representative compounds. The examples are provided to illustrate particular aspects of the disclosure and do not limit the scope of the present invention.

EXAMPLES

Scheme I:

Example 1

Synthesis of 1,2-O-isopropylidene-3-deoxy-3-(phenyl-thiourido)-α-D-glucofuranoside (Compound No. 1)

Step a: 1,2,5,6-Di-O-isopropylidene-3-O-tolyl-α-D-allofuranoside

To a solution of the compound 1,2,5,6-di-O-isopropylidene-α-D-allofuranoside (20 g, 76.92 mmol) in dichloromethane (30 ml) was added pyridine (80 ml) and N,N-dimethylaminopyridine (0.20 g, 1.64 mmol) and stirred at 0° C. To the resulting reaction mixture was added a solution of para-toluenesulphonyl chloride (29.33 g, 153.84 mmol) in dichloromethane (50 ml) dropwise at the same temperature under constant stirring. The reaction mixture was subsequently stirred at room temperature for 12 hours. The mixture was cooled to 0° C. followed by the addition of saturated solution of sodium bicarbonate till basic pH was attained. The solvent was evaporated under reduced pressure and the residue thus obtained was diluted with water under constant stirring. The solid thus obtained was filtered, washed with water, dried over anhydrous sodium sulphate and concentrated under reduced pressure to furnish the title compound. Yield: 23 g.

Step b: 1,2,5,6-Di-O-isopropylidene-3-deoxy-3-azido-α-D-glucofuranoside

To a solution of the compound obtained from step a above (23 g, 55.55 mmol) in dry dimethylformamide (150 ml) was added sodium azide (18.06 g, 277.77 mmol) under an argon atmosphere. The reaction mixture was heated to 170° C. for 12-15 hours under an argon atmosphere. The solvent was evaporated under reduced pressure, diluted with water and extracted with ethyl acetate. The organic layer was separated, washed with water, dried over anhydrous sodium sulphate and concentrated under reduced pressure. The residue thus obtained was purified by column chromatography using 5% ethyl acetate in hexane as eluent to furnish the title compound. Yield: 18 g.

Step c: 1,2,5,6-Di-O-isopropylidene-3-deoxy-3-amino-α-D-glucofuranoside

To a suspension of lithium aluminium hydride (6.91 g, 182.496 mmol) in dry distilled tetrahydrofuran (150 ml) and cooled to 0° C. was added the compound obtained from step b above (26 g, 91.228 mmol) dropwise under constant stirring at the same temperature. The reaction mixture was then stirred at room temperature for 3 hours. The reaction mixture was cooled to 0° C. followed by the addition of ethyl acetate and saturated solution of sodium sulphate dropwise. The reaction mixture was filtered through a celite pad, extracted with ethyl acetate, washed with water, dried over anhydrous sodium sulphate, filtered and concentrated under reduced pressure to furnish the title compound. Yield: 17.3 g.

Step d: 1,2,5,6-Di-O-isopropylidene-3-deoxy-3-(phenyl-thiourido)-x-D-glucofuranoside To a solution of the compound obtained from step c above (0.110 g, 0.424 mmol) in dichloromethane (4.0 ml) was added triethylamine (0.142 ml, 0.1019 mmol) and phenyl isothiocyanate (0.69 g, 0.510 mmol) and stirred the reaction mixture at room temperature for 6-7 hours. The solvent was evaporated under reduced pressure and the residue thus obtained was treated with dichloromethane and water. The organic layer was separated, dried over anhydrous sodium sulphate, filtered and concentrated under reduced pressure. The residue thus obtained was purified by column chromatography using 20% ethyl acetate in hexane as eluent to furnish the title compound.

Step e: 1,2-O-isopropylidene-3-deoxy-3-(phenyl-thiourido)-α-D-glucofuranoside

To a solution of the compound obtained from step d above (1.20 g, 0.304 mmol) in tetrahydrofuran (5 ml) was added perchloric acid (60%, 0.60 ml) at 0° C. The reaction mixture was stirred at the same temperature for 5-6 hours and subsequently a saturated sodium bicarbonate solution was added till basic pH was attained. The mixture was extracted with ethyl aceate, washed with water, dried over anhydorus sodium sulphate, filtered and concentrated under reduced pressure. The residue thus obtained was crystallized using ethyl aceate in hexane to furnish the title compound. Yield: 0.670 g.

¹H NMR (CDCl₃, 300 MHz): δ 10.26 (brs, 1H, —NH & D₂O exchangeable), 8.35 (brs, 1H, —NH & D2O exchangeable), 7.88-7.73 (m, 3H, Ar—H), 7.68-7.56 (m, 2H, Ar—H), 5.82 (d, 1H, J=3.00 Hz, —CH), 5.23 (brs, 1H, —OH & D20 exchangeable), 4.58 (d, J=3.00 Hz, —CH), 4.13-4.10 (m, 1H, —CH), 3.50-3.48 (m, 1H, —CH), 1.42 (s, 3H, —CH₃) and 1.25 (s, 3H, —CH₃).

Mass (m/z, +ve ion mode): 355 [M⁺+1].

The following illustrative analogs were prepared similarily, for example, 1,2-O-isopropylidene-3-deoxy-3-[(trifluoromethylphenyl)-thiourido]-α-D-glucofuranoside (Compound No. 2), 1,2-O-isopropylidene-3-deoxy-3-[(4-fluorophenyl)thiourido]-α-D-glucofuranoside (Compound No. 3), 1,2-O-isopropylidene-3-deoxy-3-[(4-methoxyphenyl)-thiourido]-α-D-glucofuranoside (Compound No. 4), 1,2-O-isopropylidene-3-deoxy-3-[(2,6-dimethylphenyl)-thiourido]-α-D-glucofuranoside (Compound No. 5), 1,2-O-isopropylidene-3-deoxy-3-[(2,4 dichlorophenyl)-thiourido]-α-D-glucofuranoside (Compound No. 6), 1,2-O-isopropylidene-3-deoxy-3-[(2,4-difluorophenyl)-thiourido]-α-D-glucofuranoside (Compound No. 7), 1,2-O-isopropylidene-3-deoxy-3-[(4-nitrophenyl)-thiourido]-α-D-glucofuranoside (Compound No. 9), 1,2-O-isopropylidene-3-deoxy-3-[(2-nitrophenyl)-thiourido]-α-D-glucofuranoside (Compound No. 10), 1,2-O-isopropylidene-3-deoxy-3-{[4-(4-cyclohexylpropyl)phenyl]-thiourido}-α-D-glucofuranoside (Compound No. 11), 1,2-O-isopropylidene-3-deoxy-3-[(3-nitrophenyl)-thiourido]-α-D-glucofuranoside (Compound No. 12), 1,2-O-isopropylidene-3-deoxy-3-[(3-methoxyphenyl)-thiourido]-α-D-glucofuranoside (Compound No. 63), 1,2-O-isopropylidene-3-deoxy-3-[(2-fluorophenyl)-thiourido]-α-D-glucofuranoside (Compound No. 64), and 1,2-O-isopropylidene-3-deoxy-3-[(4-cyanophenyl)-thiourido]-α-D-glucofuranoside (Compound No. 65).

Example 2

Synthesis of 1,2-O-isopropylidene-3-deoxy-3-(phenyl-thiourido)-5,6-dioxa spiro[4,5]decane-α-D-glucofuranoside (Compound No. 52)

To a solution of Compound No. 1 (0.100 g, 0.282 mmol) in dry toluene (10 ml) was added dry and powdered molecular sieves (4 A°, 0.25 g), para-toluenesulphonic acid (0.100 g, 0.525 mmol) and cyclohexanone dimethyl ketal (0.43 ml, 2.824 mmol). The reaction mixture was refluxed for 2 hours. The mixture was filtered through a celite pad and the filterate was concentrated under reduced pressure. The residue thus obtained was purified by preparative thin layer chromatography using 50% ethyl aceatate in hexane as eluent to furnish the title compound. Yield: 0.50 g.

¹H NMR (DMSO-d₆, 300 MHz): δ 9.60 (brs, 1H, —NH, —D2O exchangeable), 7.89 (brs, 1H, —NH, D2O exchangeable), 7.53-7.51 (m, 2H, Ar—H), 7.36-7.30 (m, 2H, Ar—H), 7.12-7.02 (m, 1H, Ar—H), 5.85 (d, 1H, J=3.00 Hz, —CH), 4.85 (m, 1H, —CH), 4.57 (d, 1H, J=3.00 Hz, —CH), 4.21-4.20 (m, 1H, J=3.00 Hz, —CH), 4.09-4.06 (m, 3H, —OCH₂ & —CH), 4.05-4.04 (m, 1H, —CH), 1.52-1.44 (brm, 10H, 5x-CH₂) and 1.26 (s, 6H, 2x-CH₃).

Mass (m/z, +ve ion mode): 435 [M⁺+1].

The following illustrative analogs were prepared similarily, for example, 1,2-O-isopropylidene-3-deoxy-3-[(3-nitrophenyl)-thiourido]-5,6-dioxa spiro[4,5]decane-α-D-glucofuranoside (Compound No. 8), 1,2-O-isopropylidene-3-deoxy-3-[(4-fluorophenyl)-thiourido]-5,6-dioxa spiro[4,5]decane-α-D-glucofuranoside (Compound No. 48), 1,2-O-isopropylidene-3-deoxy-3-[(2-fluorophenyl)-thiourido]-5,6-dioxa spiro[4,5]decane-α-D-glucofuranoside (Compound No. 49), 1,2-O-isopropylidene-3-deoxy-3-[(2-nitrophenyl)-thiourido]-5,6-dioxa spiro[4,5]decane-α-D-glucofuranoside (Compound No. 50), 1,2-O-isopropylidene-3-deoxy-3-[(2,6-dimethylphenyl)-thiourido]-5,6-dioxa spiro[4,5]decane-α-D-glucofuranoside (Compound No. 51), 1,2-O-isopropylidene-3-deoxy-3-[(2-methoxyphenyl)-thiourido]-5,6-dioxa spiro[4,5]decane-α-D-glucofuranoside (Compound No. 53), 1,2-O-isopropylidene-3-deoxy-3-[(2,4-difluorophenyl)-thiourido]-5,6-dioxa spiro[4,5]decane-α-D-glucofuranoside (Compound No. 54), and 1,2-O-isopropylidene-3-deoxy-3-[(4-nitrophenyl)-thiourido]-5,6-dioxa spiro[4,5]decane-α-D-glucofuranoside (Compound No. 55).

1,2-O-isopropylidene-3-deoxy-3-[(2,4-dichlorophenyl)-thiourido]-5,6-dioxa spiro[4,5]decane-α-D-glucofuranoside (Compound No. 56)

1,2-O-isopropylidene-3-deoxy-3-[(4-cyanophenyl)-thiourido]-5,6-dioxa spiro[4,5]decane-α-D-glucofuranoside (Compound No. 61)

1,2-O-isopropylidene-3-deoxy-3-{[4-(4-cyclohexylpropyl)phenyl]-thiourido}-5,6-dioxa spiro[4,5]decane-α-D-glucofuranoside (Compound No. 62)

Scheme II:

Example 3

Synthesis of 1,2-O-isopropylidene-3-deoxy-3-(phenyl-thiourido)-5,6-di-O-pentyl-α-D-glucofuranoside (Compound No. 40)

Step a: 1,2,5,6-Di-O-isopropylidene-3-O-tolyl-α-D-allofuranoside

To a solution of the compound 1,2,5,6-di-O-isopropylidene-α-D-allofuranoside (20 g, 76.92 mmol) in dichloromethane (300 ml) was added pyridine (80 ml) and N,N-dimethylaminopyridine (0.200 g, 1.639 mmol) and stirred at 0° C. To the resulting reaction mixture was added a solution of para-toluenesulphonyl chloride (29.33 g, 153.84 mmol) in dichloromethane (50 ml) dropwise at the same temperature under constant stirring. Stirred the reaction mixture further at room temperature for 12 hours. The mixture was cooled to 0° C. followed by the addition of saturated sodium bicarbonate solution till basic pH was attained. The solvent was evaporated under reduced pressure and the residue thus obtained was diluted with water under constant stirring. A white solid thus obtained was filtered, washed with water and dried under vacuum to furnish the title compound.

Step b: 1,2,5,6-Di-O-isopropylidene-3-deoxy-3-azido-α-D-glucofuranoside

To a solution of the compound obtained from step a above (23 g, 55.555 mmol) in dry dimethylformamide (150 ml) was added sodium azide (18.058 g, 277.77 mmol) under an argon atmosphere. The reaction mixture was heated to 170° C. for 12-15 hours under an argon atmosphere. The solvent was evaporated under reduced pressure, diluted with water and extracted with ethyl acetate. The organic layer was separated, washed with water, dried over anydrous sodium sulphate, filtered and evaporated under reduced pressure. The residue thus obtained was purified by column chromatography using 5% ethyl acetate in hexane as eluent to furnish the title compound.

Step c: 1,2-O-isopropylidene-3-deoxy-3-azido-5,6-dihydroxy-α-D-glucofuranoside

To an ice-cold solution of the compound obtained from step b above (6.0 g, 21.053 mmol) in tetrahydrofuran (12 ml) was added aqueous perchloric acid (60%, 4 ml) at 0° C. and stirred the reaction mixture at the same temperature for 6-7 hours. To the resulting reaction mixture was added a saturated solution of sodium bicarbonate till basic pH was attained. The mixture was extracted with ethyl acetate, washed with water, dried over anhydrous sodium sulphate, filtered and concentrated under reduced pressure. The residue thus obtained was purified by column chromatography using 50% ethyl acetate in hexane as eluent to furnish the title compound.

Step d: 1,2-O-isopropylidene-3-deoxy-3-azido-5,6-di-O-pentyl-α-D-glucofuranoside To a mixture of sodium hydride (60% dispersion in oil, 0.650 g, 16.326 mmol) in dimethylformamide (10 ml) at 0° C. was added a solution of the compound obtained from step c above (1 g, 0.408 mmol) in dimethylformamide (5 ml) dropwise at 0° C. The reaction mixture was stirred at room temperature for 1 hour and subsequently cooled to 0° C. To the resulting reaction mixture was added 1-bromopentane (2.466 g, 16.326 mmol) at the same temperature dropwise. The mixture was then heated at 90-100° C. for 6-7 hours. The solvent was evaporated under reduced pressure and the residue thus obtained was diluted with water, extracted with ethyl acetate, washed with water, dried over anhydrous sodium sulphate, filtered and concentrated under reduced pressure. The residue thus obtained was purified by column chromatography using 5% ethyl acetate in hexane as an eluent to furnish the title compound.

Step e: 1,2-O-isopropylidene-3-deoxy-3-amino-5,6-di-O-pentyl-α-D-glucofuranoside To a suspension of lithium aluminium hydride (0.197 g, 5.195 mmol) in dry tetrahydrofuran (15 ml) at 0° C. was added a solution of compound obtained from step d above (1 g, 2.597 mmol) in tetrahydrofuran (15 ml) dropwise. The reaction mixture was stirred at the same temperature for 30 min. and subsequently allowed to attain room temperature and stirred for further 30 min. The reaction mixture was cooled to 0° C. followed by the addition of ethyl acetate and a saturated solution of sodium sulphate dropwise. The reaction mixture was filtered through a celite pad, extracted with ethyl acetate, washed with water, dried over anhydrous sodium sulphate, filtered and concentrated under reduced pressure to furnish the title compound.

Step f: 1,2-O-isopropylidene-3-deoxy-3-(phenyl-thiourido)-5,6-di-O-pentyl-α-D-glucofuranoside To a solution of the compound obtained from step e above (0.110 g, 0.306 mmol) in dichloromethane (3 ml) was added triethylamine (0.128 ml, 0.919 mmol) and phenylisothiocyanate (0.049 g, 0.367 mmol). The mixture was stirred at room temperature for 6-7 hours. The solvent was evaporated under reduced pressure and the residue thus obtained was treated with dichloromethane and water. The organic layer was separated, washed with water, dried over anhydrous sodium sulphate, filtered and concentrated under reduced pressure. The residue thus obtained was purified by preparative thin layer chromatography using 20% ethyl acetate in hexane as eluent to furnish the title. Yield: 0.080 g.

$^1$H NMR (CDCl$_3$, 300 MHz): δ 8.23 (brs, 1H, —NH & D$_2$O exchangeable), 7.68 (brs, 1H, —NH & D$_2$O exchangeable), 7.41-7.37 (m, 2H, Ar—H), 7.25-7.24 (m, 1H, Ar—H), 7.23-7.15 (m, 2H, Ar—H), 5.81 (d, 1H, J=3.00 Hz, —CH), 4.98 (d, 1H, J=3.00Hz, —CH), 4.70-4.65 (m, 1H, —CH), 4.32-4.30 (m, 1H, —CH), 3.75-3.73 (m, 1H, —CH), 3.55-3.37 (m, 6H, 3x-OCH$_2$), 1.52 (s, 3H,—CH$_3$), 1.35-1.25 (m, 15H, 6x-CH$_2$ & —CH$_3$) and 0.95-0.81 (m, 6H, 2x-CH$_3$).

Mass (m/z, +ve ion mode): 495 [M$^+$+1].

The following illustrative analogs were prepared similarily, for example, 1,2-O-isopropylidene-3-deoxy-3-[(4-fluorophenyl)-thiourido]-5,6-di-O-ethyl-α-D-glucofuranoside (Compound No. 13), 1,2-O-isopropylidene-3-deoxy-3-[(2-fluorophenyl)-thiourido]-5,6-di-O-ethyl-α-D-glucofuranoside (Compound No. 14), 1,2-O-isopropylidene-3-deoxy-3-[(2-methoxyphenyl)-thiourido]-5,6-di-O-ethyl-α-D-glucofuranoside (Compound No. 15), 1,2-O-isopropylidene-3-deoxy-3-[(4-cyanophenyl)-thiourido]-5,6-di-O-ethyl-α-D-glucofuranoside (Compound No. 16), 1,2-O-isopropylidene-3-deoxy-3-[(4-trifluoromethylphenyl)-thiourido]-5,6-di-O-ethyl-α-D-glucofuranoside (Compound No. 17), 1,2-O-isopropylidene-3-deoxy-3-[(2-trifluoromethylphenyl)-thiourido]-5,6-di-O-ethyl-α-D-glucofuranoside (Compound No. 18), 1,2-O-isopropylidene-3-deoxy-3-(phenyl-thiourido)-5,6-di-O-ethyl-α-D-glucofuranoside (Compound No. 19), 1,2-O-isopropylidene-3-deoxy-3-[(4-fluorophenyl)-thiourido]-5,6-di-O-propyl-α-D-glucofuranoside (Compound No. 20), 1,2-O-isopropylidene-3-deoxy-3-[(2-fluorophenyl)-thiourido]-5,6-di-O-propyl-α-D-glucofuranoside (Compound No. 21), 1,2-O-isopropylidene-3-deoxy-3-[(2-methoxyphenyl)-thiourido]-5,6-di-O-propyl-α-D-glucofuranoside (Compound No. 22), 1,2-O-isopropylidene-3-deoxy-3-[(4-cyanophenyl)-thiourido]-5,6-di-O-propyl-α-D-glucofuranoside (Compound No. 23), 1,2-O-isopropylidene-3-deoxy-3-[(4-trifluomethylphenyl)-thiourido]-5,6-di-O-propyl-α-D-glucofuranoside (Compound No. 24), 1,2-O-isopropylidene-3-deoxy-3-[(2-trifluoromethylphenyl)-thiourido]-5,6-di-O-propyl-α-D-glucofuranoside (Compound No. 25), 1,2-O-isopropylidene-3-deoxy-3-(phenyl-thiourido)-5,6-di-O-propyl-α-D-glucofuranoside (Compound No. 26), 1,2-O-isopropylidene-3-deoxy-3-[(4-fluorophenyl)-thiourido]-5,6-di-O-butyl-α-D-glucofuranoside (Compound No. 27), 1,2-O-isopropylidene-3-deoxy-3-[(2-fluorophenyl)-thiourido]-5,6-di-O-butyl-α-D-glucofuranoside (Compound No. 28), 1,2-O-isopropylidene-3-deoxy-3-[(2-methoxyphenyl)-thiourido]-5,6-di-O-butyl-α-D-glucofuranoside (Compound No. 29), 1,2-O-isopropylidene-3-deoxy-3-[(4-cyanophenyl)-thiourido]-5,6-di-O-butyl-α-D-glucofuranoside (Compound No. 30), 1,2-O-isopropylidene-3-deoxy-3-[(4-trifluoromethylphenyl)-thiourido]-5,6-di-O-butyl-α-D-glucofuranoside (Compound No. 31), 1,2-O-isopropylidene-3-deoxy-3-[(2-trifluoromethylphenyl)-thiourido]-5,6-di-O-butyl-α-D-glucofuranoside (Compound No. 32), 1,2-O-isopropylidene-3-deoxy-3-(phenyl-thiourido)-5,6-di-O-butyl-α-D-glucofuranoside (Compound No. 33), 1,2-O-isopropylidene-3-deoxy-3-[(4-fluorophenyl)-thiourido]-5,6-di-O-pentyl-α-D-glucofuranoside (Compound No. 34), 1,2-O-isopropylidene-3-deoxy-3-[(2-fluorophenyl)-thiourido]-5,6-di-O-pentyl-α-D-glucofuranoside (Compound No. 35), 1,2-O-isopropylidene-3-deoxy-3-[(2-methoxyphenyl)-thiourido]-5,6-di-O-pentyl-α-D-glucofuranoside (Compound No. 36), 1,2-O-isopropylidene-3-deoxy-3-[(4-cyanophenyl)-thiourido]-5,6-di-O-pentyl-α-D-glucofuranoside (Compound No. 37), 1,2-O-isopropylidene-3-deoxy-3-[(4-trifluoromethylphenyl)-thiourido]-5,6-di-O-pentyl-α-D-glucofuranoside (Compound No. 38), 1,2-O-isopropylidene-3-deoxy-3-[(2-trifluoromethylphenyl)-thiourido]-5,6-di-O-pentyl-α-D-glucofuranoside (Compound No. 39), 1,2-O-isopropylidene-3-deoxy-3-[(4-fluorophenyl)-thiourido]-5,6-di-O-hexyl-α-D-glucofuranoside (Compound No. 41), 1,2-O-isopropylidene-3-deoxy-3-[(2-fluorophenyl)-thiourido]-5,6-di-O-hexyl-α-D-glucofuranoside (Compound No. 42), 1,2-O-isopropylidene-3-deoxy-3-[(2-methoxyphenyl)-thiourido]-5,6-di-O-hexyl-α-D-glucofuranoside (Compound No. 43), 1,2-O-isopropylidene-3-deoxy-3-[(4-cyanophenyl)-thiourido]-5,6-di-O-hexyl-α-D-glucofuranoside (Compound No. 44), 1,2-O-isopropylidene-3-deoxy-3-[(4-trifluoromethylphenyl)-thiourido]-5,6-di-O-hexyl-α-D-glucofuranoside (Compound No. 45), 1,2-O-isopropylidene-3-deoxy-3-[(2-trifluoromethylphenyl)-thiourido]-5,6-di-O-hexyl-α-D-glucofuranoside (Compound No. 46), and 1,2-O-isopropylidene-3-deoxy-3-(phenyl-thiourido)-5,6-di-O-hexyl-α-D-glucofuranoside (Compound No. 47).

Example 4

Synthesis of 1,2-O-isopropylidene-3-deoxy-3-[(2-chloro-4-fluorophenyl)-amido]-5,6-di-O-pentyl-α-D-glucofuranoside (Compound No. 57)

To a solution of the compound 1,2-O-isopropylidene-3-deoxy-3-amino-5,6-di-O-pentyl-α-D-glucofuranoside (0.100 g, 0.278 mmol) in dry dimethylformamide (3 ml) was added N-methylmorpholine (0.084 g, 0.834 mmol) and 2-chloro-4-fluorophenylacetic acid. The mixture was stirred at room temperature for 10 minutes. To the resulting reaction mixture was added 1-hydroxybenzotriazole (0.075 g, 0.556 mmol) and stirred the mixture at room temperature for 1 hour. To it was added 1-(3-dimethylaminopropyl)-3-ethylcarbodiimide hydrochloride (0.106 g, 0.556 mmol) at 0° C. and stirred at the same temperature for 1 hour and subsequently at room temperature for 12 hours. The reaction mixture was poured into water, extracted with ethyl acetate, washed with water, dried over anhydrous sodium sulphate, filtered and concentrated under reduced pressure. The residue thus obtained was purified by preparative thin layer chromatography using 30% ethyl acetate in hexane as eluent to furnish the title compound. Yield: 0.080 g.

$^1$H NMR (CDCl$_3$, 300 MHz): δ 8.09 (brs, 1H, —NH), 7.54-7.29 (m, 1H, Ar—H), 7.15-7.13 (m, 1H, Ar—H), 5.78 (d, 1H, J=3.00 Hz, —CH), 4.62 (d, 1H, J=3.00 Hz, —CH), 4.26-4.25 (m, 1H, —CH), 4.20 (m, 1H, —CH), 3.90 (m, 2H, 2x-CH), 3.60 (s, 2H, —CH$_2$Ph), 3.48-3.36 (m, 6H, 3x-OCH$_2$), 1.48-1.22 (brm, 18H, 6x-CH$_2$ & 2x-CH$_3$) and 0.91-0.87 (m, 6H, -2x-CH$_3$).

Mass (m/z, +ve ion mode): 530 [M$^+$+1].

The following illustrative compounds were prepared similarly, for example, 1,2-O-isopropylidene-3-deoxy-3-[(2,4-difluorophenyl)-amido]-5,6-di-O-pentyl-α-D-glucofuranoside (Compound No. 58), 1,2-O-isopropylidene-3-deoxy-3-[(2,4-difluorophenyl)-amido]-5,6-di-O-hexyl-α-D-glucofuranoside (Compound No. 59), and 1,2-O-isopropylidene-3-deoxy-3-[(2-chloro-4-fluorophenyl)-amido]-5,6-di-O-hexyl-α-D-glucofuranoside (Compound No. 60).

Pharmacological Activity

The compounds of the present invention are tested in one or both of the assays described herein. Standard assays are used to evaluate activity of compounds in present invention on inflammatory cells. Attenuation of agonist-induced release of lipid mediator of neutrophil chemotaxis, leukotriene B4 (LTB$_4$), is used to evaluate inhibitory effect on neutrophils.

A23187 Induced LTB$_4$ Release

Venous blood was collected from healthy human donors using heparin as an anti-coagulant. Neutrophils were isolated from freshly drawn blood after dextran sedimentation and ficoll separation (*Eur. J. Biochem.* 169, 175, 1987). 180 μl of the of neutrophil suspension (0.2×10$^6$cells/ml) was taken and added 19 μL of Hank's Buffer salt solution along with 1 μL of the test drug (200 times concentrated) in a 24 well plate and incubated at 37° C. for 1 hour. 3 minutes before the end of test compound incubation, 0.25 mM Ca$^{++}$/Mg$^{++}$ were added. Then, 0.3 μg/ml A23187 (Sigma Chem, USA) was added and incubated for further 10 min at 37° C. The reaction was stopped by adding 80 μL of cold methanol and centrifuged to remove cell debris (*J Pharmacol Exp Ther.* 297:267, 2001). The samples were analysed for LTB$_4$ release using LTB$_4$ ELISA kits (Assay Design Inc., USA). The amount of LTB$_4$ released was quantified and percent inhibition of LTB$_4$ release was calculated with respect to the difference between the A23187 stimulated and negative control cells, to compute IC$_{50}$ values. In vitro data obtained on particular examples of the disclosed compounds (Nos. 2,9, 17,47,48,55,62 and 63) shows IC$_{50}$ values of from about 700 nM to about 10 μM.

Assay for 5-Lipoxygenase Activity

In a 96 well UV-plate, 100 μl of phosphate buffer saline (PBS) containing DTT (200 μM), ATP (100 μM) and calcium chloride (100 μM) was added. To each well 0.5 μl of test drug (200 times concentrated) or vehicle was added, followed by 4 μl of recombinant 5-Lox (3 units/μl) and was incubated at 37° C. for 5 min. The reaction was initiated by adding 1 μl of 1 mM freshly prepared arachidonic acid and increase in absorbance was monitored at 236 nm for 10 min. (*J. Biol. Chem.*

261:11512, 1986). A plot of absorbance verses time curve was prepared and area under curve (AUC) was computed for each well. Percent inhibition of AUC for different treatments was calculated with respect to the difference between the arachidonic acid stimulated and negative control values, to compute $IC_{50}$ values.

In vitro data obtained on particular examples of the disclosed compounds (Nos. 1-7, 9-24, 26, 28-29, 31-43, 45, 47-50, 52-55, and 61-66) shows $IC_{50}$ values of from about 260 nM to about 10 μM, for example, from about 260 nM to about 4.5 μM, or, for example, from about 260 nM to about 2.0 μM, or, for example, from about 260 nM to about 1.3 μM, or, for example, from about 260 μM to about 800 nM.

We claim:
1. A compound selected from the group consisting of:
1,2-O-isopropylidene-3-deoxy-3-(phenyl-thiourido)-α-D-glucofuranoside (Compound No. 1),
1,2-O-isopropylidene-3-deoxy-3-[(trifluoromethylphenyl)-thiorido]-α-D-glucofuranoside (Compound No. 2),
1,2-O-isopropylidene-3-deoxy-3-[(4-fluorophenyl)-thiourido]-α-D-glucofuranoside (Compound No. 3),
1,2-O-isopropylidene-3-deoxy-3-[(4-methoxyphenyl)-thiourido]-α-D-glucofuranoside (Compound No. 4),
1,2-O-isopropylidene-3-deoxy-3-[(2,6-dimethylphenyl)-thiourido]-α-D-glucofuranoside (Compound No. 5),
1,2-O-isopropylidene-3-deoxy-3-[(2,4-dichlorophenyl)-thiourido]-α-D-glucofuranoside (Compound No. 6),
1,2-O-isopropylidene-3-deoxy-3-[(2,4-difluorophenyl)-thiourido]-α-D-glucofuranoside (Compound No. 7),
1,2-O-isopropylidene-3-deoxy-3-[(3-nitrophenyl)-thiourido]-5,6-dioxa spiro[4,5]decane-α-D-glucofuranoside (Compound No. 8),
1,2-O-isopropylidene-3-deoxy-3-[(4-nitrophenyl)-thiourido]-α-D-glucofuranoside (Compound No. 9),
1,2-O-isopropylidene-3-deoxy-3-[(2-nitrophenyl)-thiourido]-α-D-glucofuranoside (Compound No. 10),
1,2-O-isopropylidene-3-deoxy-3-{[4-(4-cyclohexylpropyl)phenyl]-thiourido}-α-D-glucofuranoside (Compound No. 11),
1,2-O-isopropylidene-3-deoxy-3-[(3-nitrophenyl)-thiourido]-α-D-glucofuranoside (Compound No. 12),
1,2-O-isopropylidene-3-deoxy-3-[(4-fluorophenyl)-thiourido]-5,6-di-O-ethyl-α-D-glucofuranoside (Compound No. 13),
1,2-O-isopropylidene-3-deoxy-3-[(2-fluorophenyl)-thiourido]-5,6-di-O-ethyl-α-D-glucofuranoside (Compound No. 14),
1,2-O-isopropylidene-3-deoxy-3-[(2-methoxyphenyl)-thiourido]-5,6-di-O-ethyl-α-D-glucofuranoside (Compound No. 15),
1,2-O-isopropylidene-3-deoxy-3-[(4-cyanophenyl)-thiourido]-5,6-di-O-ethyl-α-D-glucofuranoside (Compound No. 16),
1,2-O-isopropylidene-3-deoxy-3-[(4-trifluoromethylphenyl)-thiourido]-5,6-di-O-ethyl-α-D-glucofuranoside (Compound No. 17),
1,2-O-isopropylidene-3-deoxy-3-[(2-trifluoromethylphenyl)-thiourido]-5,6-di-O-ethyl-α-D-glucofuranoside (Compound No. 18),
1,2-O-isopropylidene-3-deoxy-3-(phenyl-thiourido)-5,6-di-O-ethyl-α-D-glucofuranoside (Compound No.19),
1,2-O-isopropylidene-3-deoxy-3-[(4-fluorophenyl)-thiourido]-5,6-di-O-propyl-α-D-glucofuranoside (Compound No. 20),
1,2-O-isopropylidene-3-deoxy-3-[(2-fluorophenyl)-thiourido]-5,6-di-O-propyl-α-D-glucofuranoside (Compound No. 21),
1,2-O-isopropylidene-3-deoxy-3-[(2-methoxyphenyl)-thiourido]-5,6-di-O-propyl-α-D-glucofuranoside (Compound No. 22),
1,2-O-isopropylidene-3-deoxy-3-[(4-cyanophenyl)-thiourido]-5,6-di-O-propyl-α-D-glucofuranoside (Compound No. 23),
1,2-O-isopropylidene-3-deoxy-3-[(4-trifluoromethylphenyl)-thiourido]-5,6-di-O-propyl-α-D-glucofuranoside (Compound No. 24),
1,2-O-isopropylidene-3-deoxy-3-[(2-trifluoromethylphenyl)-thiourido]-5,6-di-O-propyl-α-D-glucofuranoside (Compound No. 25),
1,2-O-isopropylidene-3-deoxy-3-(phenyl-thiourido)-5,6-di-O-propyl-α-D- glucofuranoside (Compound No. 26),
1,2-O-isopropylidene-3-deoxy-3-[(4-fluorophenyl)-thiourido]-5,6-di-O-butyl-α-D-glucofuranoside (Compound No. 27),
1,2-O-isopropylidene-3-deoxy-3-[(2-fluorophenyl)-thiourido]-5,6-di-O-butyl-α-D-glucofuranoside (Compound No. 28),
1,2-O-isopropylidene-3-deoxy-3-[(2-methoxyphenyl)-thiourido]-5,6-di-O-butyl-α-D-glucofuranoside (Compound No. 29),
1,2-O-isopropylidene-3-deoxy-3-[(4-cyanophenyl)-thiourido]-5,6-di-O-butyl-α-D-glucofuranoside (Compound No. 30),
1,2-O-isopropylidene-3-deoxy-3-[(4-trifluoromethylphenyl)-thiourido]-5,6-di-O-butyl-α-D-glucofuranoside (Compound No. 31),
1,2-O-isopropylidene-3-deoxy-3-[(2-trifluoromethylphenyl)-thiourido]-5,6-di-O-butyl-α-D-glucofuranoside (Compound No. 32),
1,2-O-isopropylidene-3-deoxy-3-(phenyl-thiourido)-5,6-di-O-butyl-α-D- glucofuranoside (Compound No. 33),
1,2-O-isopropylidene-3-deoxy-3-[(4-fluorophenyl)-thiourido]-5,6-di-O-pentyl-α-D-glucofuranoside (Compound No. 34),
1,2-O-isopropylidene-3-deoxy-3-[(2-fluorophenyl)-thiourido]-5,6-di-O-pentyl-α-D-glucofuranoside (Compound No. 35),
1,2-O-isopropylidene-3-deoxy-3-[(2-methoxyphenyl)-thiourido]-5,6-di-O-pentyl-α-D-glucofuranoside (Compound No. 36),
1,2-O-isopropylidene-3-deoxy-3-[(4-cyanophenyl)-thiourido]-5,6-di-O-pentyl-α-D-glucofuranoside (Compound No. 37),
1,2-O-isopropylidene-3-deoxy-3-[(4-trifluoromethylphenyl)-thiourido]-5,6-di-O-pentyl-α-D-glucofuranoside (Compound No. 38),
1,2-O-isopropylidene-3-deoxy-3-[(2-trifluoromethylphenyl)-thiourido]-5,6-di-O-pentyl-α-D-glucofuranoside (Compound No. 39),
1,2-O-isopropylidene-3-deoxy-3-(phenyl-thiourido)-5,6-di-O-pentyl-α-D-glucofuranoside (Compound No. 40),
1,2-O-isopropylidene-3-deoxy-3-[(4-fluorophenyl)-thiourido]-5,6-di-O-hexyl-α-D-glucofuranoside (Compound No. 41),
1,2-O-isopropylidene-3-deoxy-3-[(2-fluorophenyl)-thiourido]-5,6-di-O-hexyl-α-D-glucofuranoside (Compound No. 42),
1,2-O-isopropylidene-3-deoxy-3-[(2-methoxyphenyl)-thiourido]-5,6-di-O-hexyl-α-D-glucofuranoside (Compound No. 43),

1,2-O-isopropylidene-3-deoxy-3-[(4-cyanophenyl)-thiourido]-5,6-di-O-hexyl-α-D-glucofuranoside (Compound No. 44), 1,2-O-isopropylidene-3-deoxy-3-[(4-trifluoromethylphenyl)-thiourido]-5,6-di-O-hexyl-α-D-glucofuranoside (Compound No. 45), 1,2-O-isopropylidene-3-deoxy-3-[(2-trifluoromethylphenyl)-thiourido]-5,6-di-O-hexyl-α-D-glucofuranoside (Compound No. 46), 1,2-O-isopropylidene-3-deoxy-3-(phenyl-thiourido)-5,6-di-O-hexyl-α-D-glucofuranoside (Compound No. 47), 1,2-O-isopropylidene-3-deoxy-3-[(4-fluorophenyl)-thiourido]-5,6-dioxa spiro[4,5]decane-α-D-glucofuranoside (Compound No. 48), 1,2-O-isopropylidene-3-deoxy-3-[(2-fluorophenyl)-thiourido]-5,6-dioxa spiro[4,5]decane-α-D-glucofuranoside (Compound No. 49), 1,2-O-isopropylidene-3-deoxy-3-[(2-nitrophenyl)-thiourido]-5,6-dioxa spiro[4,5]decane-α-D-glucofuranoside (Compound No. 50), 1,2-O-isopropylidene-3-deoxy-3-[(2,6-dimethylphenyl)-thiourido]-5,6-dioxa spiro[4,5]decane-α-D-glucofuranoside (Compound No. 51), 1,2-O-isopropylidene-3-deoxy-3-(phenyl-thiourido)-5,6-dioxa spiro[4,5]decane-α-D-glucofuranoside (Compound No. 52), 1,2-O-isopropylidene-3-deoxy-3-[(2-methoxyphenyl)-thiourido]-5,6-dioxa spiro[4,5]decane-α-D-glucofuranoside (Compound No. 53), 1,2-O-isopropylidene-3-deoxy-3-[(2,4-difluorophenyl)-thiourido]-5,6-dioxa spiro[4,5]decane-α-D-glucofuranoside (Compound No. 54), 1,2-O-isopropylidene-3-deoxy-3-[(4-nitrophenyl)-thiourido]-5,6-dioxa spiro[4,5]decane-α-D-glucofuranoside (Compound No. 55), 1,2-O-isopropylidene-3-deoxy-3-[(2,4-dichlorophenyl)-amido]-5,6-dioxa spiro[4,5]decane-α-D-glucofuranoside (Compound No. 56), 1,2-O-isopropylidene-3-deoxy-3-[(2-chloro-4-fluorophenyl)-amido]-5,6-di-O-pentyl-α-D-glucofuranoside (Compound No. 57), 1,2-O-isopropylidene-3-deoxy-3-[(2,4-difluorophenyl)-amido]-5,6-di-O-pentyl-α-D-glucofuranoside (Compound No. 58), 1,2-O-isopropylidene-3-deoxy-3-[(2,4-difluorophenyl)-amido]-5,6-di-O-hexyl-α-D-glucofuranoside (Compound No. 59), 1,2-O-isopropylidene-3-deoxy-3-[(2-chloro-4-fluorophenyl)-thiourido]-5,6-di-O-pentyl-α-D-glucofuranoside (Compound No. 60), 1,2-O-isopropylidene-3-deoxy-3-[(4-cyanophenyl)-thiourido]-5,6-dioxa spiro[4,5]decane-α-D-glucofuranoside (Compound No. 61), 1,2-O-isopropylidene-3-deoxy-3-{[4-(4-cyclohexylpropyl)phenyl]-thiourido}-5,6-dioxa spiro[4,5]decane-α-D-glucofuranoside (Compound No. 62), 1,2-O-isopropylidene-3-deoxy-3-[(3-methoxyphenyl)-thiourido]-α-D-glucofuranoside (Compound No. 63), 1,2-O-isopropylidene-3-deoxy-3-[(2-fluorophenyl)-thiourido]-α-D-glucofuranoside (Compound No. 64), 1,2-O-isopropylidene-3-deoxy-3-[(4-cyanophenyl)-thiourido]-α-D-glucofuranoside (Compound No. 65), and 1,2-O-isopropylidene-3-deoxy-3-[(4-trifluoromethylphenyl)-thiourido]-5,6-dioxa spiro[4,5]decane-α-D-glucofuranoside (Compound No. 66).

2. A pharmaceutical composition comprising a compound of claim 1 and a pharmaceutically acceptable carrier.

* * * * *